(12) United States Patent
Bachovchin et al.

(10) Patent No.: US 7,459,428 B2
(45) Date of Patent: *Dec. 2, 2008

(54) METHOD OF REGULATING GLUCOSE METABOLISM, AND REAGENTS RELATED THERETO

(75) Inventors: William W. Bachovchin, Melrose, MA (US); Andrew G. Plaut, Lexington, MA (US); Daniel Drucker, Toronto (CA)

(73) Assignees: Trustees of Tufts College, Medford, MA (US); New England Medical Center Hospitals, Inc., Boston, MA (US); 1149336 Ontario, Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/487,947

(22) Filed: Jul. 17, 2006

(65) Prior Publication Data

US 2007/0129314 A1 Jun. 7, 2007

Related U.S. Application Data

(63) Continuation of application No. 10/794,316, filed on Mar. 4, 2004, now Pat. No. 7,078,381, which is a continuation of application No. 10/190,267, filed on Jul. 3, 2002, now Pat. No. 6,890,898, which is a continuation of application No. 09/628,225, filed on Jul. 28, 2000, now Pat. No. 7,157,429, which is a continuation of application No. PCT/US99/02294, filed on Feb. 2, 1999.

(60) Provisional application No. 60/073,409, filed on Feb. 2, 1998.

(51) Int. Cl.
*A61K 38/04* (2006.01)

(52) U.S. Cl. ............... 514/2; 514/18; 514/19; 514/119; 514/423; 514/626

(58) Field of Classification Search ............... None
See application file for complete search history.

(56) References Cited

U.S. PATENT DOCUMENTS

| 4,522,752 A | 6/1985 | Sisto et al. |
| 5,061,811 A | 10/1991 | Pinori et al. |

(Continued)

FOREIGN PATENT DOCUMENTS

| DE | 19616486 | 10/1997 |

(Continued)

OTHER PUBLICATIONS

Balkan et al., "Improved insulin secretion and oral glucose tolerance after in vivo inhibition of DPP-IV in obese Zucker rats," Diabetologia Suppl. 40, A131 Abstract (1997).

(Continued)

*Primary Examiner*—Jeffrey E Russel
(74) *Attorney, Agent, or Firm*—Dana M. Gordon; Foley Hoag LLP

(57) ABSTRACT

One aspect of the present invention relates to a method for treating Type II diabetes in an animal, comprising conjointly administering to the animal metformin and an inhibitor of dipeptidylpeptidase IV or a pharmaceutically acceptable salt thereof in an amount sufficient to treat Type II diabetes of the animal.

24 Claims, 6 Drawing Sheets

U.S. PATENT DOCUMENTS

| | | | |
|---|---|---|---|
| 5,631,224 | A | 5/1997 | Efendic et al. |
| 5,783,556 | A | 7/1998 | Clark et al. |
| 5,834,428 | A | 11/1998 | Drucker et al. |
| 5,952,301 | A | 9/1999 | Drucker et al. |
| 6,011,155 | A | 1/2000 | Villhauer |
| 6,184,201 | B1 | 2/2001 | Drucker et al. |
| 6,803,357 | B1 | 10/2004 | Bachovchin et al. |
| 6,890,898 | B2 * | 5/2005 | Bachovchin et al. ............ 514/2 |
| 7,078,381 | B2 * | 7/2006 | Bachovchin et al. ............ 514/2 |
| 7,157,429 | B1 * | 1/2007 | Bachovchin et al. ........... 514/18 |

FOREIGN PATENT DOCUMENTS

| | | |
|---|---|---|
| WO | WO 89/03223 | 4/1989 |
| WO | WO 93/08259 | 4/1993 |
| WO | WO 95/15309 | 6/1995 |
| WO | WO 96/14857 | 5/1996 |
| WO | WO 96/39385 | 12/1996 |
| WO | WO 97/40832 | 11/1997 |
| WO | WO 98/19998 | 5/1998 |
| WO | WO 98/25644 | 6/1998 |
| WO | WO 00/10549 | 3/2000 |
| WO | WO 01/14318 | 3/2001 |
| WO | WO 01/34594 | 5/2001 |
| WO | WO 01/81337 | 11/2001 |

OTHER PUBLICATIONS

Bell et al., "Exon duplication and divergence in the human preproglucagon gene," Nature 304 (5924):368-71 (1983).

Bell et al., "Hamster preproglucagon contains the sequence of glucagon and two related peptides," Nature 302(5910):716-8 (1983).

Conlon, J.M., "Proglucagon-derived peptides: nomenclature, biosynthetic relationships and physiological roles," Diabetolgia 31(8):563-6 (1988).

Coruzzi et al., "Gastric antisecretory activity of telenzepine, a new MI-selective muscarinic antagonist: com-parison with pirenzepine," Arch Int Pharmacodyn Ther 302:232-41 (1989).

Coutts et al., "Structure-Activity Relationships of Boronic Acid Inhibitors of Dipeptidyl Peptidase IV I. Variation of the P2 Position of Xaa-boroPro Dipeptides," J. Med. Chem. 39: 2087-2094 (1996).

Deacon et al., "Both subcutaneously and intrave-nously administered glucagon-like peptide I are rapidly degraded from the NH2-terminus in type II diabetic patients and in healthy subjects," Diabetes 44(9):1126-31 (1995).

Deacon et al., "Dipeptidyl peptidase IV inhibition potentiates the insulinotropic effect of glucagon-like peptide 1 in the anesthetized pig," Diabetes, vol. 47:764-769 (1998).

Deacon et al., "Degradation of Glucagon-Like Peptide-1 by Human Plasma in Vitro Yields an N-Terminally Truncated Peptide that is a Major Endogenous Metabolite in Vivo," J. Clin. Endocrin. 83:952-957 (1995).

Dupre, "Influences of the gut on the endocrine pan-creas," The Endocrine Pancreas (Raven Press, New York) pp. 253-281 (1991).

Ebert et al., "Gastrointestinal peptides and insulin secretion," Diabetes Met. Rev. 3:1-26 (1987).

Gutniak et al., "Antidiabetogenic effect of glucagon-like peptide-1 (7-36) amide in normal subjects and patients with diabetes mellitus", N Engl JMed 326(20):1316-22 (1992).

Habener et al., "Biosyntesies of glucagon" The Endo-crine Pancreas (Raven Press, New York) pp. 53-71 (1991).

Holst, J. J. & Deacon, C.F., "Inhibition of the Activity of Dipeptidyl-Peptidase IV as a Treatment for Type 2 Diabetes," Diabetes 47:1663-1670 (1998).

Holst et al., "Truncated glucagon-like peptide I, an insulin-releasing hormone from the distal gut," FEBS Lett. 211(2):169-74 (1987).

Kawashima et al., "Pharmacological differentiation of presynaptic MI muscarinic receptors modulating acetylcho-line release from postsynaptic muscarinic receptors in guinea-pig ileum," Gen Pharmacol 21(1):17-21 (1990).

Kieffer et al., "Degradation of Glucose-Dependent Inulinotropic Polypeptide and Truncated Glucagon-Like Peptide 1 in Vitro and in Vivo by Dipeptidyl Peptidase IV," Endocrin. 136, 3585-3596 (1995).

Kinder et al., "Acylamino boronic acids and difluoroborane ana-logues of amino acids: potent inhibitors of chymotrypsin and elastase," JMed Chem 28(12):1917-25 (1985).

Kreymann et al., "Glucagon-like peptide-1 7-36: a physiological incretin in man," Lancet 2(8571):1300-4 (1987).

Kubiak et al., "Metabolism or mouse growth hor-mone-releasing factor, mGRF(142)OH, and selected ana-logs from the bovine GRF series in mouse and bovine plasma in vitro," Pept Res 7(3):153-61 (1994).

Lambrecht et al., "Pharmacology of hexahydro-difenidol, hexahydro-sila-difenidol and related selective muscarinic antago-nists," Trends Pharmacol Sci 10(Suppl):60 (1989).

Lund et al., "Pancreatic preproglucagon cDNA con-tains two glucagon-related coding sequences arranged in tandem," Proc Mad Acad Sci USA 79(2):345-9 (1982).

Matteson et al., "Synthesis and properties of pinanediol ∀-amino boronic acids," Organometallics 3:1284 (1984).

Mentlein et al., "Dipeptidyl-peptidase IV hydrolyses gastric inhibi-tory polypeptide, glucagon-like peptide-1(736)amide, peptide histidine methionine and is responsible for their degradation in human serum," Eur. J. Biochem. 214, 829-835 (1993).

Mentlein et al., "Proteolytic processing of neuropeptide Y and peptide YY by dipeptidyl peptidase IV," Regulatory Peptides 49:133-144 (Dec. 10, 1993).

Mojsov et al., "Preproglucagon gene expression in pancreas and intestine diversifies at the level of post-trans-lational processing," J Biol Chem 261(25):11880-9 (1986).

Mojsov et al., "Insulinotropin: glucagon-like peptide 1(7-37) co-encoded in the glucagon gene is a potent stimu-lator of insulin release in the perfused rat pancreas," J Clin Invest 79(2);616-9 (1987).

Mojsov, S., "Structural requirements for biological activ-ity of glucagon-like peptide-l," Int J Pept Protein Res 40(3-4):333-43 (1992).

Orskov et al., "Pancreatic and intestinal processing of proglucagon in man," Diabetologia 30(11):874-81 (1987).

Patzelt et al., "Identification and processing of proglucagon in pan-creatic islets," Nature 282(5736):260-6 (1979).

Pederson et al., "Improved Glucose Tolerance in Zucker Fatty Rats by Oral Admintration of the Dipeptidyl Peptidase IV Inhibitor Isoleucine Thiazolidide," Diabetes 47, 1253-1258 (Aug. 1998).

Pospisilik, John A. et al., "Metabolism of Glucagon by Dipeptidyl Peptidase IV (CD26)," Regulatory Peptides 96:133-141 (2001).

Radhakrishna et al., "New method for direct conver-sion of amides to amines," J Org Chem 44:1746 (1979).

Schmidt et al., "Glucagon-like peptide-1 but not glucagon-like peptide-2 stimulates insulin release from iso-lated rat pancreatic Islets," Diabetologia 28(9):704-7 (1985).

Shue et al., "Amine bond surrogates: a general syn-thetic route to trans carbon-carbon double bond isosteres," Tetrahedron Letters 28:3225 (1987).

Stanley et al., "Repeated hypothalamic stimulation with neuropeptide Y increases daily carbohydrate and fat intake and body weight gain in female rats," Physiol Behav 46(2):173-7(19890.

Weir et al., "Glucagonlike peptide I (7-37) actions on endocrine pancrease," Diabetes 38(3):338-42 (1989).

Wilding et al., "Increased neuropeptide Y content in individual hypo-thalamic nuclei, but not neuropeptide Y mRNA, in diet-induced obesity in rats," J. Endocrinol 132(2):299-304 (1992).

* cited by examiner

METHOD OF REGULATING GLUCOSE METABOLISM, AND REAGENTS RELATED THERETO

This Application is a continuation of U.S. patent application Ser. No. 10/794,316, filed Mar. 4, 2004, now U.S. Pat. No. 7,078,381; which is a continuation of U.S. patent application Ser. No. 10/190,267, filed Jul. 3, 2002, now U.S. Pat. No. 6,890,898; which is a continuation of U.S. patent application Ser. No. 09/628,225, filed Jul. 28, 2000 now U.S. Pat. No. 7,157,429; which is a continuation of PCT/US99/02294, filed Feb. 2, 1999; which claims the benefit of priority under 35 U.S.C. § 119(e) to U.S. Provisional Patent Application Ser. No. 60/073,409, filed Feb. 2, 1998.

FUNDING

Work described herein was supported by funding from the National Institutes of Health. The United States Government has certain rights in the invention.

BACKGROUND OF THE INVENTION

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%); and to fat (30-40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs. Fat formation is a major pathway for carbohydrate utilization.

The net effect of insulin is to promote the storage and use of carbohydrates, protein and fat. Insulin deficiency is a common and serious pathologic condition in man. In insulin-dependent (IDDM or Type I) diabetes the pancreas produces little or no insulin, and insulin must be injected daily for the survival of the diabetic. In noninsulin-dependent (NIDDM or Type II) diabetes the pancreas retains the ability to produce insulin and in fact may produce higher than normal amounts of insulin, but the amount of insulin is relatively insufficient, or less than fully effective, due to cellular resistance to insulin.

Diabetes mellitus (DM) is a major chronic illness found in humans with many consequences. Some complications arising from long-standing diabetes are blindness, kidney failure, and limb amputations. Insulin-dependent diabetes mellitus (IDDM) accounts for 10 to 15% of all cases of diabetes mellitus. The action of IDDM is to cause hyperglycemia (elevated blood glucose concentration) and a tendency towards diabetic ketoacidosis (DKA). Currently treatment requires chronic administration of insulin. Non-insulin dependent diabetes mellitus (NIDDM) is marked by hyperglycemia that is not linked with DKA. Sporadic or persistent incidence of hyperglycemia can be controlled by administering insulin. Uncontrolled hyperglycemia can damage the cells of the pancreas which produce insulin (the β-islet cells) and in the long term create greater insulin deficiencies. Currently, oral sulfonylureas and insulin are the only two therapeutic agents available in the United States. for treatment of Diabetes mellitus. Both agents have the potential for producing hypoglycemia as a side effect, reducing the blood glucose concentration to dangerous levels. There is no generally applicable and consistently effective means of maintaining an essentially normal fluctuation in glucose levels in DM. The resultant treatment attempts to minimize the risks of hypoglycemia while keeping the glucose levels below a target value. The drug regimen is combined with control of dietary intake of carbohydrates to keep glucose levels in control.

In either form of diabetes there are widespread abnormalities. In most NIDDM subjects, the fundamental defects to which the abnormalities can be traced are (1) a reduced entry of glucose into various "peripheral" tissues and (2) an increased liberation of glucose into the circulation from the liver. There is therefore an extracellular glucose excess and an intracellular glucose deficiency. There is also a decrease in the entry of amino acids into muscle and an increase in lipolysis. Hyperlipoproteinemia is also a complication of diabetes. The cumulative effect of these diabetes-associated abnormalities is severe blood vessel and nerve damage.

Endocrine secretions of pancreatic islets are regulated by complex control mechanisms driven not only by blood-borne metabolites such as glucose, amino acids, and catecholamines, but also by local paracrine influences. Indeed, pancreatic α- and β-cells are critically dependent on hormonal signals generating cyclic AMP (cAMP) as a synergistic messenger for nutrient-induced hormone release. The major pancreatic islet hormones, glucagon, insulin and somatostatin, interact with specific pancreatic cell types to modulate the secretory response. Although insulin secretion is predominantly controlled by blood glucose levels, somatostatin inhibits glucose-mediated insulin secretion.

The human hormone glucagon is a polypeptide hormone produced in pancreatic A-cells. The hormone belongs to a multi-gene family of structurally related peptides that include secretin, gastric inhibitory peptide, vasoactive intestinal peptide and glicentin. These peptides variously regulate carbohydrate metabolism, gastrointestinal motility and secretory processing. However, the principal recognized actions of pancreatic glucagon are to promote hepatic glycogenolysis and glyconeogenesis, resulting in an elevation of blood sugar levels. In this regard, the actions of glucagon are counter regulatory to those of insulin and may contribute to the hyperglycemia that accompanies Diabetes mellitus (Lund et al. (1982) *PNAS*, 79:345-349).

Preproglucagon, the zymogen form of glucagon, is translated from a 360 base pair gene and is processed to form proglucagon (Lund, et al., supra). Patzelt, et al. (*Nature*, 282: 260-266 (1979)) demonstrated that proglucagon is further processed into glucagon and a second peptide. Later experiments demonstrated that proglucagon is cleaved carboxyl to Lys-Arg or Arg-Arg residues (Lund et al., supra; and Bell et al. (1983) *Nature* 302:716-718). Bell et al. also discovered that proglucagon contained three discrete and highly homologous peptide regions which were designated glucagon, glucagon-like peptide 1 (GLP-1), and glucagon-like peptide 2 (GLP-2). GLP-1 has attracted increasing attention as a humoral stimulus of insulin secretion. In humans, this 29-amino acid peptide, cleaved from proglucagon by cells of the intestinal mucosa, is released into the circulation after nutrient intake (Holst et al. (1987) *FEBS Lett* 211:169; Orskov et al. (1987) *Diabetologia* 30:874; Conlon J (1988) *Diabetologia* 31:563).

GLP-1 has been found to be a glucose-dependent insulinotropic agent (Gutniak et al. (1992) *N. Engl. J. Bled.* 326: 1316-1322). GLP-1 is now known to stimulate insulin secretion (insulinotropic action) causing glucose uptake by cells which decreases serum glucose levels (see, e.g., Mojsov, S., Int. J. Peptide Protein Research, 40:333-343 (1992)). For instance, it has been shown to be a potent insulin secretagogue in experimental models and when infused into humans (Gutniak et al., supra; Mojsov et al. (1988) *J Clin Invest* 79:616; Schmidt et al. (1985) *Diabetologia* 28:704; and Kreymann et al. (1987) *Lancet* 2:1300). Thus, GLP-1 is a candidate for the role of an "incretin", having augmentary effects on glucose-mediated insulin release.

It is also noted that numerous GLP-1 analogs have been demonstrated which demonstrate insulinotropic action are known in the art. These variants and analogs include, for example, GLP-1(7-36), $Gln_9$-GLP-1(7-37), D-$Gln_9$-GLP-1(7-37), acetyl-$Lys_9$-GLP-1(7-37), $Thr_{16}$-$Lys_{18}$-GLP-1(7-37), and $Lys_{18}$-GLP-1(7-37). Derivatives of GLP-1 include, for example, acid addition salts, carboxylate salts, lower alkyl esters, and amides (see, e.g., WO91/11457).

OBJECTS OF THE INVENTION

It is one object of this invention to provide improved methods for reducing in animal subjects (including humans) in need of such treatment at least one of insulin resistance, hyperinsulinemia, and hyperglycemia and abating Type II diabetes. Another object is to provide improved methods for reducing at least one of body fat stores, hyperlipidemia, hyperlipoproteinemia, and for abating atherosclerosis. It is another object of this invention to provide methods for interfering with glucose and/or lipid metabolism in a manner beneficial to the host.

It is yet another object of this invention to provide improved methods for the long-term reduction and abatement of at least one of the foregoing disorders based on a therapeutic regimen administered over the short-term.

It is still another object of the present invention to provide a method for regulating, and altering on a long term basis, the glucose and lipogenic responses of vertebrate animals, including humans.

In particular, it is an object of the invention to provide methods for producing long lasting beneficial changes in one or more of the following: the sensitivity of the cellular response of a species to insulin (reduction of insulin resistance), blood insulin levels, hyperinsulinemia, blood glucose levels, the amount of body fat stores, blood lipoprotein levels, and thus to provide effective treatments for diabetes, obesity and/or atherosclerosis.

DETAILED DESCRIPTION OF THE INVENTION

Figure 1:
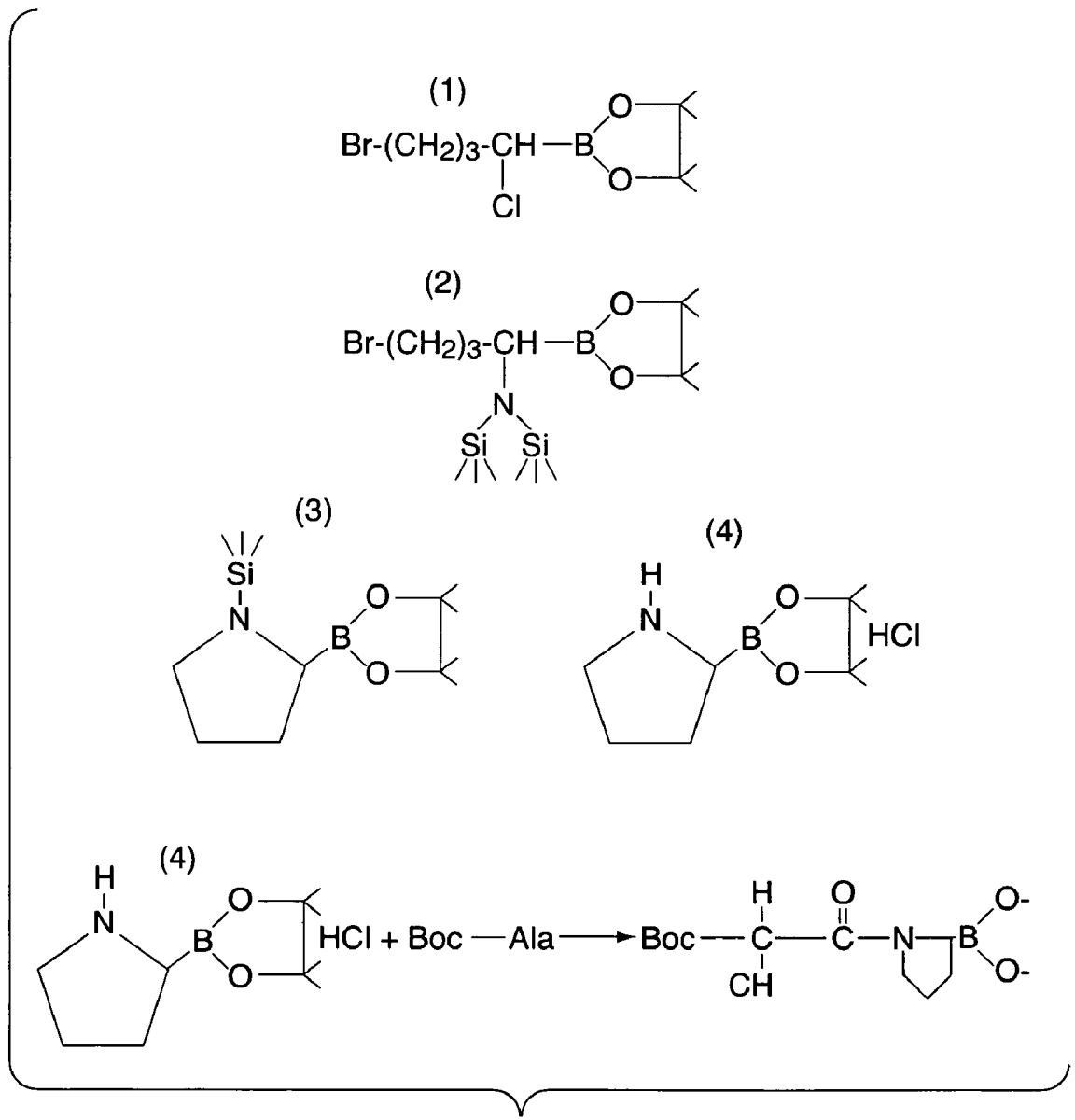
FIG. 1 is a diagrammatic representation of the synthesis of a boro proline compound.

Glucose-induced insulin secretion is modulated by a number of hormones and neurotransmitters. In particular, two gut hormnones, glucagon-like peptide-1 (GLP-1) and gastric inhibitory peptide (GIP) are insulinotropic agents, e.g., being agents which can stimulate, or cause the stimulation of, the synthesis or expression of the hormone insulin, are thus called gluco-incretins (Dupre, in *The Endocrine Pancreas,* E. Samois Ed. (Raven Press, New York, (1991), 253-281); and Ebert et al. (1987) *Diabetes Metab. Rev.* p3). Glucagon-like peptide-1 is a glucoincretin both in man and other mammals (Dupre et al. supra, and Kreymann et al. (1987) *Lancet* 2:300). It is part of the preproglucagon molecule (Bell et al. (1983) *Nature* 304:368) which is proteolytically processed in intestinal L cells to GLP-1(1-37) and GLP-1(7-36)amide or GLP-1(7-37) (Mojsov et al. (1986) *J. Biol. Chem.* 261:11880; and Habener et al.: *The Endocrine Pancreas,* E. Samois Ed. (Raven Press, New York (1991), 53-71). Only the truncated forms of GLP-1 are biologically active and both have identical effects on insulin secretion in beta cells (Mojsov et al. (1987) *J. Clin. Invest* 79:616; and Weir et al. (1989) *Diabetes* 38:338). They are the most potent gluco-incretins so far described and are active at concentrations as low as one to ten picomolar.

The metabolic fate of exogenous GLP-1 has been studied in nondiabetic and type II diabetic subjects. Subcutaneous and intravenous GLP-1 are both rapidly degraded in a time-dependent manner, for instance, having a half-life in diabetic patients of substantially less than 30 minutes. See, for example, Deacon et al. (1995) *Diabetes* 44:1126-1131.

i. Overview of the Invention

The. present invention provides methods and compositions for modification and regulation of glucose and lipid metabolism, generally to reduce insulin resistance, hyperglycemia, hyperinsulinemia, obesity, hyperlipidemia, hyperlipoprotein-emia (such as chylomicrons, VLDL and LDL), and to regulate body fat and more generally lipid stores, and, more generally, for the improvement of metabolism disorders, especially those associated with diabetes, obesity and/or atherosclerosis. As described in greater detail below, the subject method includes the administration, to an animal, of a composition including one or more dipeptidylpeptidase inhibitors, especially inhibitors of the dipeptidylpeptidase IV. (DPIV) enzyme or other enzyme of similar specificity, which are able to inhibit the proteolysis of GLP-1 and accordingly increase the plasma half-life of that hormone.

Preferably, the compounds utilized in the subject method will produce an EC50 for the desired biological effect of at least one, two, three and even four orders of magnitude less than the EC50 for that compound as an immunosuppressant. Indeed, a salient feature of such compounds as the peptidyl boronates is that the inhibitors can produce, for example, an EC50 for inhibition of glucose tolerance in the nanomolar or less range, whereas the compounds have EC50's for immunosuppression in the µM or greater range. Thus, a favorable therapeutic index can be realized with respect to the unwanted sideeffect of immunosuppression.

While not wishing to bound by any particular theory, it is observed that compounds which inhibit DPIV are, correlatively, able to improve glucose tolerance, though not necessarily through mechanisms involving DPIV inhibition per se. Indeed, the results described in Example 6 (and FIG. 5) demonstrating an effect in mice lacking a GLP-1 receptor suggest that the subject method may not include a mechanism of action directly implicating GLP-1 itself, though it has not been ruled out that GLP-1 may have other receptors. However, in light of the correlation with DPIV inhibition, in preferred embodiments, the subject method utilizes an agent with a Ki for DPIV inhibition of 1.0 nm or less, more preferably of 0.1 nm or less, and even more preferably of 0.01 nM or less. Indeed, inhibitors with Ki values in the picomolar and even femtamolar range are contemplated. Thus, while the active agents are described herein, for convience, as "DPIV inhibitors", it will be understood that such nomenclature is not intending to limit the subject invention to a particular mechanisim of action.

For instance, in certain embodiments the method involves administration of a DPIV inhibitor, preferably at a predetermined time(s) during a 24-hour period, in an amount effective to improve one or more aberrant indices associated with glucose metabolism disorders (e.g., glucose intolerance, insulin resistance, hyperglycemia, hyperinsulinemia and Type II diabetes).

In other embodiments, the method involves administration of a DPIV inhibitor in an amount effective to improve aberrant indices associated with obesity. Fat cells-release the hormone leptin, which travels in the bloodstream to the brain and, through leptin receptors there, stimulates production of GLP-1. GLP-1, in turn, produces the sensation of being full. The leading theory is that the fat cells of most obese people probably produce enough leptin, but leptin may not be able to properly engage the leptin receptors in the brain, and so does not stimulate production of GLP-1. There is accordingly a great deal of research towards utilizing preparations of GLP-1 as an apepitite suppressant. The subject method provides a means for increasing the half-life of both endogenous and ectopically added GLP-1 in the treatment of disorders associated with obesity.

In a more general sense, the present invention provides methods and compositions for altering the pharmokinetics of a variety of different polypeptide hormones by inhibiting the proteolysis of one or more peptide hormones by DPIV or some other proteolytic activity. Post-secretory metabolism is an important element in the overall homeostasis of regulatory peptides, and the other enzymes involved in these processes may be suitable targets for pharmacological intervention by the subject method.

For example, the subject method can be used to increase the half-life of other proglucagon-derived peptides, such as glicentin (corresponding to PG 1-69), oxyntomodulin (PG 33-69), glicentin-related pancreatic polypeptide (GRPP, PG 1-30), intervening peptide-2 (IP-2, PG 111-122amide), and glucagon-like peptide-2 (GLP-2, PG 126-158).

GLP-2, for example, has been identified as a factor responsible for inducing proliferation of intestinal epithelium. See, for example, Drucker et al. (1996) *PNAS* 93:7911. The subject method can be used as part of a regimen for treating injury, inflammation or resection of intestinal tissue, e.g., where enhanced growth and repair of the intestinal mucosal epithelial is desired.

DPIV has also been implicated in the metabolism and inactivation of growth hormone-releasing factor (GHRF). GHRF is a member of the family of homologous peptides that includes gluicagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) *Peptide Res* 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

Likewise, the DPIV inhibitors of the subject invention can be used to alter the plasma half-life of secretin, VIP, PHI, PACAP, GIP and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

Another aspect of the present invention relates to pharmaceutical compositions of dipeptidylpeptidase inhibitors, particularly DPIV inhibitors, and their uses in treating and/or preventing disorders which can be improved by altering the homeostasis of peptide hormones. In a preferred embodiment, the inhibitors have hypoglycemic and antidiabetic activities, and can be used in the treatment of disorders marked by abberrant glucose metabolism (including storage). In particular embodiments, the compositions of the subject methods are useful as insulinotropic agents, or to potentiate the insulinotropic effects of such molecules as GLP-1. In this regard, the present method can be useful for the treatment and/or prophylaxis of a variety of disorders, including one or more of: hyperlipemia, hyperglycemia, obesity, glucose tolerance insufficiency, insulin resistance and diabetic complications.

In general, the inhibitors of the subject method will be small molecules, e.g., with molecular weights less than 7500 amu, preferably less than 5000 amu, and even more preferably less than 2000 amu and even 1000 amu. In preferred embodiments, the inhibitors will be orally active.

In certain embodiments, the subject inhibitors are peptidyl compounds (including peptidomimetics) which are optimized, e.g., generally by selection of the Cα substituents, for the substrate specificity of the targeted proteolytic activity. These peptidyl compounds will include a functional group, such as in place of the scissile peptide bond, which facilitates inhibition of a serine-, cysteine- or aspartate-type protease, as appropriate. For example, the inhibitor can be a peptidyl α-diketone or a peptidyl α-keto ester, a peptide haloalkylketone, a peptide sulfonyl fluoride, a peptidyl boronate, a peptide epoxide, a peptidyl diazomethanes, a peptidyl phosphonate, isocoumarins, benzoxazin-4-ones, carbamates, isocyantes, isatoic anhydrides or the like. Such functional groups have bee provided in other protease inhibitors, and general routes for their synthesis are known. See, for example, Angelastro et al., *J. Med Chem.* 33:11-13 (1990); Bey et al., EPO 363,284; Bey et al., EPO 364,344; Grubb et al., WO 88/10266; Higuchi et al., EPO 393,457; Ewoldt et al., *Molecular Immunology* 29(6):713-721 (1992); Hernandez et al., *Journal of Medicinal Chemistry* 35(6): 1121-1129 (1992); Vlasak et al., *J Virology* 63(5):2056-2062 (1989); Hudig et al., *J Immunol* 147(4):1360-1368 (1991); Odakc et al., *Biochemistry* 30(8):2217-2227 (1991); Vijayalakshmi et al., *Biochemistry* 30(8):2175-2183 (1991); Kam et al., *Thrombosis and Haemostasis* 64(1):133-137 (1990); Powers et al., *J Cell Biochem* 39(1):33-46 (1989); Powers et al., Proteinase Inhibitors, Barrett et al., Eds., Elsevier, pp. 55-152 (1986); Powers et al., Biochemistry 29(12):3108-3118 (1990); Oweida et al., *Thrombosis Research* 58(2):391-397 (1990); Hudig et al., *Molecular Immunology* 26(8):793-798 (1989); Orlowski et al., *Archives of Biochemistry and Biophysics* 269(1):125-136 (1989); Zunino et al., *Biochimica et Biophysica Acta.* 967(3):331-340 (1988); Kam et al., *Biochemistry* 27(7):2547-2557 (1988); Parkes et al., *Biochem J.* 230:509-516 (1985); Green et al., *J. Biol. Chem.* 256:1923-1928 (1981); Angliker et al., *Biochem. J.* 241:871-875 (1987); Puri et al., *Arch. Biochem. Biophys.* 27:346-358 (1989); Hanada et al., Proteinase Inhibitors: Medical and Biological Aspects, Katunuma et al., Eds., Springer-Verlag pp.25-36 (1983); Kajiwara et al., *Biochem. Int.* 15:935-944 (1987); Rao et al., *Thromb. Res.* 47:635-637 (1987); Tsujinaka et al., *Biochem. Biophys. Res. Commun.* 153:1201-1208 (1988)). See also U.S. Pat. Nos. 4,935,493; 5,462,928; to Bachovchin et al., U.S. Pat. No. 5,543,396; to Powers et al., Pat. No. 5,296,604; to Hanko et al., and the PCT publication of Ferring PCT/GB94/02615.

In other embodiments, the inhibitor is a non-peptidyl compound, e.g., which can be identified by such drug screening assays as described herein. These inhibitors can be, merely to illustrate, synthetic organics, natural products, nucleic acids or carbohydrates.

A representative class of compounds for use in the method of the present invention are represented by the general formula;

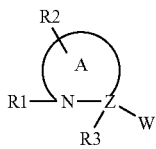

wherein

A represents a 4-8 membered heterocycle including the N and the Cα carbon;

Z represents C or N;

W represents a functional group which reacts with an active site residue of the targeted protease, as for example, —CN, —CH=NR$_5$,

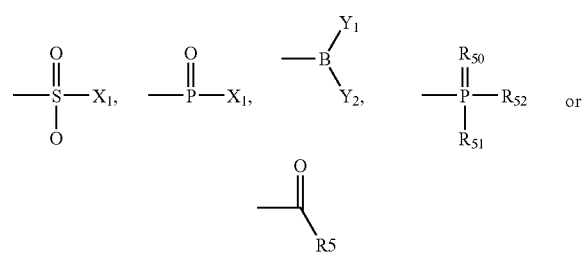

R$_1$ represents a C-terminally linked amino acid residue or amino acid analog, or a C-terminally linked peptide or peptide analog, or an amino-protecting group, or

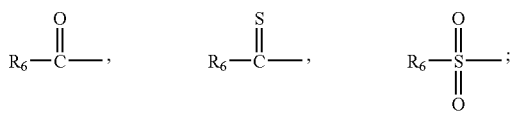

R$_2$ is absent or represents one or more substitutions to the ring A, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioforrnate), an amino, an acylamino, an amido, a cyano, a nitro, an azido, a sulfate, a sulfonate, a sulfonamnido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$;

if X is N, R$_3$ represents hydrogen, if X is C, R$_3$ represents hydrogen or a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amnido, a cyano, a nitro, an azido, a sulfate, a sulfonate, a sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$;

R$_5$ represents H, an alkyl, an alkenyl, an alkynyl, —C(X$_1$)(X$_2$)X$_3$, —(CH$_2$)m-R$_7$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_7$, —C(O)C(O)NH$_2$, —C(O)C(O)OR'$_7$;

R$_6$ represents hydrogen, a halogen, a alkyl, a alkenyl, a alkynyl, an aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$, R$_7$ represents, for each occurrence, a substituted or unsubstituted aryl, aralkyl, cycloalkyl, cycloalkenyl, or heterocycle;

R'$_7$ represents, for each occurrence, hydrogen, or a substituted or unsubstituted alkyl, alkenyl, aryl, aralkyl, cycloalkyl, cycloalkenyl, or heterocycle; and Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure (such as pinacol or the like), R$_{50}$ represents O or S;

R$_{51}$ represents N$_3$, SH$_2$, NH$_2$, NO$_2$ or OR'$_7$;

R$_{52}$ represents hydrogen, a lower alkyl, an amine, OR'$_7$, or a pharmnaceutically acceptable salt, or R$_{51}$ and R$_{52}$ taken together with the phosphorous atom to which they are attached complete a heterocyclic ring having from 5 to 8 atoms in the ring structure X$_1$ represents a halogen;

X$_2$ and X$_3$ each represent a hydrogen or a halogen m is zero or an integer in the range of 1 to 8; and n is an integer in the range of 1 to 8.

In preferred embodiments, the ring A is a 5, 6 or 7 membered ring, e.g., represented by the formula

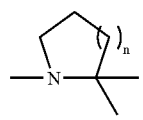

and more preferably a 5 or 6 membered ring. The ring may, optionally, be further substituted.

In preferred embodiments, W represents

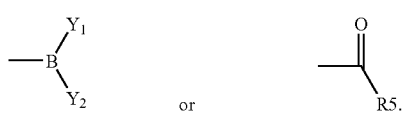

In preferred embodiments, R1 is

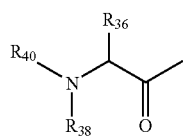

wherein R36 is a small hydrophobic group, e.g., a lower alkyl or a halogen and R38 is hydrogen, or, R36 and R37 together form a 4-7 membered heterocycle including the N and the Cα carbon, as defined for A above; and R40 represents a C-terminally linked amino acid residue or amino acid analog, or a C-terminally linked peptide or peptide analog, or an amino-protecting group In preferred embodiments, R2 is absent, or represents a small hydrophobic group such as a lower alkyl or a halogen.

In preferred embodiments, R3 is a hydrogen, or a small hydrophobic group such as a lower alkyl or a halogen.

In preferred embodiments, R5 is a hydrogen, or a halogenated lower alkyl.

In preferred embodiments, X1 is a fluorine, and X2 and X3, if halogens, are fluorine.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

Longer peptide sequences are needed for the inhibition of certain proteases and improve the specificity of the inhibition in some cases.

In preferred embodiments, the subject method utilizes, as a DPIV inhibitor, a boronic acid analogs of an amino acid. For example, the present invention contemplates the use of boroprolyl derivatives in the subject method. Exemplary boronic acid derived inhibitors of the present invention are represented by the general formula:

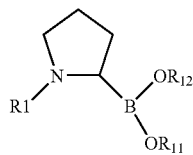

wherein $R_1$ represents a C-terminally linked amino acid residue or amino acid analog, or a terminally linked peptide or peptide analog, or

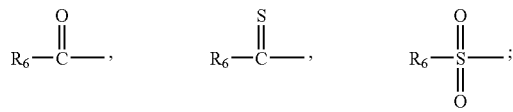

C—

$R_6$ represents hydrogen, a halogen, a alkyl, a alkenyl, a alkynyl, an aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$,

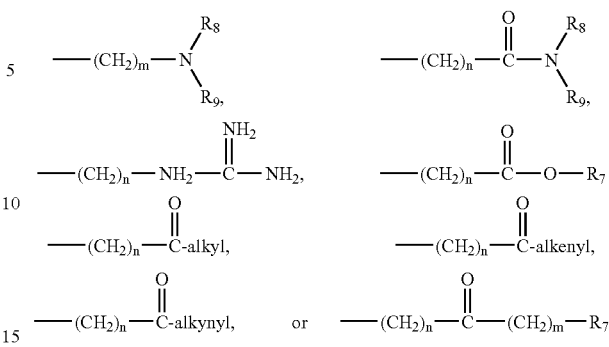

$R_7$ represents an aryl, a cycloalkyl, a cycloalkenyl, or a heterocycle;

$R_8$ and $R_9$ each independently represent hydrogen, alkyl, alkenyl, —(CH$_2$)$_m$—R$_7$, —C(=O)-alkyl, —C(=O)-alkenyl, —C(=O)-alkynyl, —C(=O)—(CH$_2$)$_m$—R$_7$, or $R_8$ and $R_9$ taken together with the N atom to which they are attached complete a heterocyclic ring having from 4 to 8 atoms in the ring structure;

$R_{11}$ and $R_{12}$ each independently represent hydrogen, a alkyl, or a pharmaceutically acceptable salt, or $R_{11}$ and $R_{12}$ taken together with the O—B—O atoms to which they are attached complete a heterocyclic ring having from 5 to 8 atoms in the ring structure;

m is zero or an integer in the range of 1 to 8; and n is an integer in the range of 1 to 8.

In other embodiments, the subject DPIV inhibitors include an aldehyde analogs of proline or. prolyl derivatives. Exemplary aldehyde-derived inhibitors of the present invention are represented by the general formula:

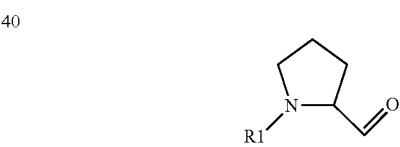

wherein $R_1$ represents a C-terminally linked amino acid residue or amino acid analog, or a terminally linked peptide or peptide analog, or

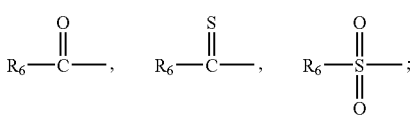

C—

$R_6$ represents hydrogen, a halogen, a alkyl, a alkenyl, a alkynyl, an aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$,

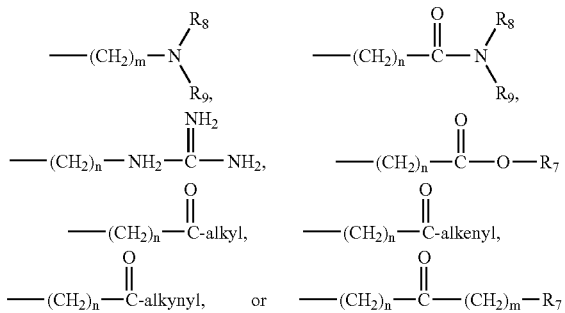

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocyclic ring having from 4 to 8 atoms in the ring structure; and m is zero or an integer in the range of 1 to 8; and n is an integer in the range of 1 to 8.

In yet further embodiments, the subject DPIV inhibitors are halo-methyl ketone analogs of an amino acid. Exemplary inhibitors of this class include compounds represented by the general formula:

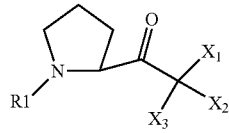

wherein $R_1$ represents a C-terminally linked amino acid residue or amino acid analog, or a terminally linked peptide or peptide analog, or

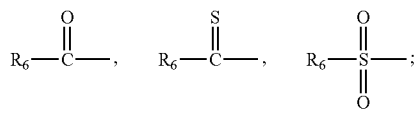

C—

$R_6$ represents hydrogen, a halogen, a alkyl, a alkenyl, a alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$,

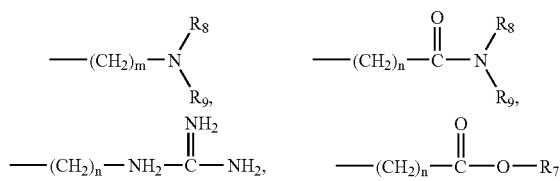

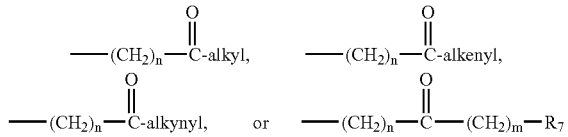

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —C(=O)-alkyl, —C(=O)-alkenyl, —C(=O)-alkynyl, C(=O)—$(CH_2)_m$—$R_7$, or $R_8$ and $R_9$ taken together with the N atom to which they are attached complete a heterocyclic ring having from 4 to 8 atoms in the ring structure;

$X_1$, $X_2$ and $X_3$ each represent a hydrogen or a halogen; and m is zero or an integer in the range of 1 to 8; and n is an integer in the range of 1 to 8.

In preferred embodiments, the DPIV inhibitor is a peptide or peptidomimetic including a prolyl group or analog thereof in the P1 specificity position, and a nonpolar amino acid in the P2 specificity position, e.g., a nonpolar amino acid such as alanine, leucine, isoleucine, valine, proline, phenylalanine, tryptophan or methionine, or an analog thereof. For example, the DPIV inhibitor may include an Ala-Pro or Pro-Pro dipeptide sequence or equivalent thereof, and be represented in the general formulas:

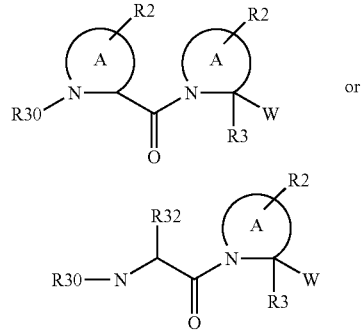

In preferred embodiments, the ring A is a 5, 6 or 7 membered ring, e.g., represented by the formula

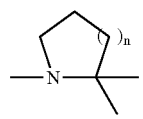

In preferred embodiments, R32 is a small hydrophobic group, e.g., a lower alkyl or a halogen.

In preferred embodiments, R30 represents a C-terminally linked amino acid residue or amino acid analog, or a C-terminally linked peptide or peptide analog, or an amino-protecting group.

In preferred embodiments, R2 is absent, or represents a small hydrophobic group such as a lower alkyl or a halogen.

In preferred embodiments, R3 is a hydrogen, or a small hydrophobic group such as a lower alkyl or a halogen.

Another representative class of compounds for use in the subject method include peptide and peptidomimetics of (D)-

Ala-(L)-Ala, e.g., preserving the diasteromeric orientation. Such inhibitors include compounds represented by the general formula:

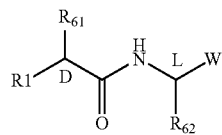

wherein

W represents a functional group which reacts with an active site residue of the targeted protease, as for example, —CN, —CH=NR$_5$,

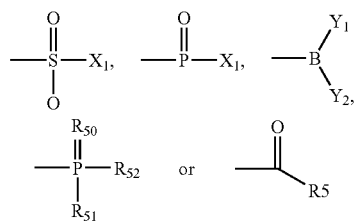

R$_1$ represents a C-terminally linked amino acid residue or amino acid analog, or a C-terminally linked peptide or peptide analog, or an amino-protecting group, or

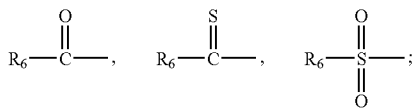

R$_3$ represents hydrogen or a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$;

R$_5$ represents H, an alkyl, an alkenyl, an alkynyl, —C(X$_1$)(X$_2$)X$_3$, —(CH$_2$)m-R$_7$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_7$, —C(O)C(O)NH$_2$, —C(O)C(O)OR'$_7$;

R$_6$ represents hydrogen, a halogen, a alkyl, a alkenyl, a alkynyl, an aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$, R$_7$ represents, for each occurrence, a substituted or unsubstituted aryl, aralkyl, cycloalkyl, cycloalkenyl, or heterocycle;

R'$_7$ represents, for each occurrence, hydrogen, or a substituted or unsubstituted alkyl, alkenyl, aryl, aralkyl, cycloalkyl, cycloalkenyl, or heterocycle;

R$_{61}$, and R$_{62}$, indepedently, represent small hydrophobic groups;

Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure (such as pinacol or the like), R$_{50}$ represents O or S;

R$_{51}$ represents N$_3$; SH$_2$, NH$_2$, NO$_2$ or OR'$_7$;

R$_{52}$ represents hydrogen, a lower alkyl, an amine, OR'$_7$, or a pharmaceutically acceptable salt, or R$_{51}$ and R$_{52}$ taken together with the phosphorous atom to which they are attached complete a heterocyclic ring having from 5 to 8 atoms in the ring structure X$_1$ represents a halogen;

X$_2$ and X$_3$ each represent a hydrogen or a halogen m is zero or an integer in the range of 1 to 8; and n is an integer in the range of 1 to 8.

In preferred embodiments, R1 is

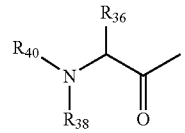

wherein R36 is a small hydrophobic group, e.g., a lower alkyl or a halogen and R38 is hydrogen, or, R36 and R37 together form a 4-7 membered heterocycle including the N and the Cα carbon, as defined for A above; and R40 represents a C-terminally linked amino acid residue or amino acid analog, or a C-terminally linked peptide or peptide analog, or an amino-protecting group.

In preferred embodiments, R3 is a hydrogen, or a small hydrophobic group such as a lower alkyl or a halogen.

In preferred embodiments, R5 is a hydrogen, or a halogenated lower alkyl.

In preferred embodiments, X1 is a fluorine, and X2 and X3, if halogens, are fluorine.

In preferred embodiments, R$_{61}$ and R$_{62}$, independently, represent lower alkyls, such as methyl, ethyl, propyl, isopropyl, tert-butyl or the like.

Also included are such peptidomimetics as olefins, phosphonates, aza-amino acid analogs and the like.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

As used herein, the definition of each expression, e.g. alkyl, m, n, etc., when it occurs more than once in any structure, is intended to be independent of its definition elsewhere in the same structure.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the subject compound which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject compounds are also readily prepared by conventional procedures such as treating an acid of Formnula I with an appropriate amount of a base such as an alkali or alkaline earth methyl hydroxide (e.g. sodium, potassium, lithium, calcium or magnesium) or an organic base such as an amine, piperidine, pyrrolidine, benzylamine and the like, or a quaternary ammonium hydroxide such as tetramethylainmonium hydroxide and the like.

Contemplated equivalents of the compounds described above include compounds which otherwise correspond thereto, and which have the same general properties thereof (e.g. the ability to inhibit proteolysis of GLP-1 or other peptide hormone or precursor thereof), wherein one or more simple variations of substituents are made which do not adversely affect the efficacy of the compound in use in the contemplated method. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

ii. Definitions

For convenience, before further description of the present invention, certain terms employed in the specification, examples, and appended claims are collected here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and mote preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbdnyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls. cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

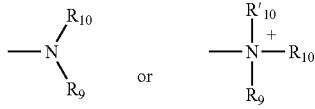

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

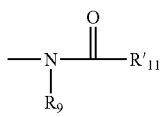

wherein R9 is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

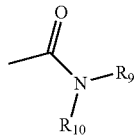

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

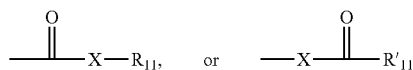

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}$' is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

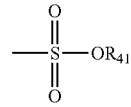

in which $R_{41}$ is an electron pair, hydrogen, alkyl, cycloalkyl, or aryl.

The term "sulfate" is art recognized and includes a moiety that can be represented by the general formula:

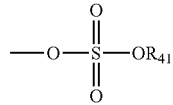

in which $R_{41}$ is as defined above.

The term "sulfonamido" is art recognized and includes a moiety that can be represented by the general formula:

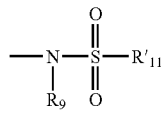

in which $R_9$ and $R'_{11}$ are as defined above.

The term "sulfamoyl" is art-recognized and includes a moiety that can be represented by the general formula:

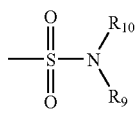

in which $R_9$ and $R_{10}$ are as defined above.

The terms "sulfoxido" or "sulfinyl", as used herein, refers to a moiety that can be represented by the general formula:

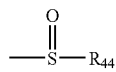

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

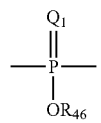

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

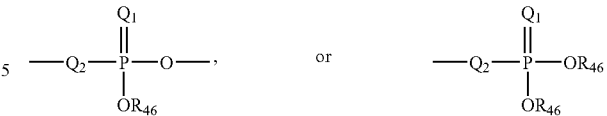

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphdrothioate".

A "phosphoramidite" can be represented in the general formula:

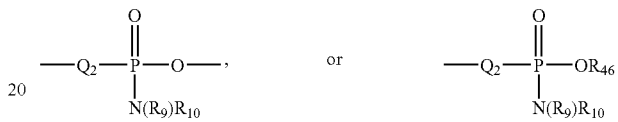

wherein $R_9$ and $R_{10}$ are as defined above, and $Q_2$ represents O, S or N.

A "phosphonamidite" can be represented in the general formula:

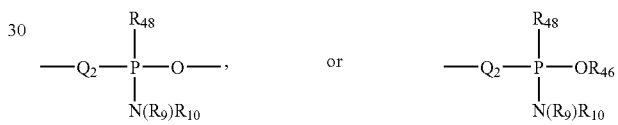

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatorns such as nitrogen may have hydrogen substituents and/or any permissible substituents of organic compounds described herein which satisfy the valencies of the heteroatoms. This invention is not intended to be limited in any manner by the permissible substituents of organic compounds.

A "small" substituent is one of 10 atoms or less.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term. "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H— (the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid residue further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC).

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

A compound is said to have an "insulinotropic activity" if it is able to stimulate, or cause the stimulation of, the synthesis or expression of the hormone insulin.

iii. Exemplary Formulations

A. Agonism of GLP-1 Effects

The inhibitors useful in the subject methods possess, in certain embodiments, the ability to lower blood glucose levels, to relieve obesity, to alleviate impaired glucose tolerance, to inhibit hepatic glucose neogenesis, and to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

Diabetes mellitus is a disease characterized by hyperglycemia occurring from a relative or absolute decrease in insulin secretion, decreased insulin sensitivity or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose; the patient's physiological response to the glucose challenge is evaluated. Generally, this is accomplished by determining the patient's blood glucose levels (the concentration of glucose in the patient's plasma, serum or whole blood) for several predetermined points in time.

As described in the appended examples, we demonstrate that, in vivo, high affinity inhibitors of DPIV are biologically active with respect to regulation of glucose metabolism. For example, a single injection of the inhibitor Pro-boro-Pro (see examples for structure) was alone sufficient to improve glucose control. A single injection of Pro-boro-Pro was also observed to potentiate the response to a subtherapeutic dose of GLP-1. We have also observed that chronic (>5 days) treatment with Pro-boro-Pro alone lowers both fasting blood sugars, and the glycemic excursion to oral glucose challenge.

As indicated above, the inhibitors useful in the subject method can be peptide- or peptidomimetic-derived inhibitors of the target proteolytic activity, or can be a non-peptide compound identified, e.g., by drug screening assays described herein. With respect to DPIV inhibitors, a salient feature of the subject method is the unexpected finding that certain DPIV inhibitors have antidiabetic activity at concentrations significantly lower than the EC50 of the compound as an immnunosuppressant. Thus, an animal can be dosed under a regimen designed to provide a blood serum concentration of inhibitor at or about the EC50 for antidiabetic effects, and still be sufficiently below the EC50 for immunosuppressive activity so as to avoid complications resulting from that activity. Indeed, for certain of the subject inhibitors, it is anticipated that dosing can be at least an order of magnitude or more greater than the antidiabetic EC50, yet still remain sufficiently below a dose producing any significant immunosuppression.

As discussed further below, a variety of assays are available in the art for identifying potential inhibitors of DPIV and the like, as well as assessing the various biological activities (including side-effects and toxicity) of such an inhibitor.

B. Agonism of Other Peptide Hormones

In another embodiment, the subject agents can be used to agonize (e.g., mimic or potentiate) the activity of other polypeptide hormones.

To illustrate, the present invention provides a method for agonizing the action of GLP-2. It has been determined that GLP-2 acts as a trophic agent, to promote growth of gastrointestinal tissue. The effect of GLP-2 is marked particularly by increased growth of the small bowel, and is therefore herein referred to as an "intestinotrophic" effect.

In still other embidiments, the subject method can be used to increase the half-life of other proglucagon-derived peptides, such as glicentin, oxyntomodulin, glicentin-related pancreatic polypeptide (GRPP), and/or intervening peptide-2 (IP-2). For example, glicentin has been demonstrated to cause proliferation of intestinal mucosa and also inhibits a peristalsis of the stomach, and has thus been elucidated as useful as a therapeutic agent for digestive tract diseases, thus leading to the present invention.

Thus, in one aspect, the present invention relates to therapeutic and related uses of DPIV inhibitors for promoting the growth and proliferation of gastrointestinal tissue, most particularly small bowel tissue. For instance, the subject method can be used as part of a regimen for treating injury, inflammation or resection of intestinal tissue, e.g., where enhanced growth and repair of the intestinal mucosal epithelial is desired.

With respect to small bowel tissue, such growth is measured conveniently as a increase in small bowel mass and length, relative to an untreated control. The effect of subject inhibitors on small bowel also manifests as an increase in the height of the crypt plus villus axis. Such activity is referred to herein as an "intestinotrophic" activity. The efficacy of the subject method may also be detectable as an increase in crypt cell proliferation and/or a decrease in small bowel epithelium apoptosis. These cellular effects may be noted most significantly in relation to the jejunum, including the distal jejunum and particularly the proximal jejunum, and also in the distal ileum. A compound is considered to have "intestinotrophic effect" if a test animal exhibits significantly increased small bowel weight, increased height of the crypt plus villus axis, or increased crypt cell proliferation or decreased small bowel epithelium apoptosis when treated with the compound (or genetically engineered to express it themselves). A model suitable for determining such gastrointestinal growth is described by U.S. Pat. No. 5,834,428.

In general, patients who would benefit from either increased small intestinal mass and consequent increased small bowel mucosal function are candidates for treatment by the subject method. Particular conditions that may be treated include the various forms of sprue including celiac sprue which results from a toxic reaction to α-gliadin from wheat, and is marked by a tremendous loss of villae of the bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the treatment may be monitored by enteric biopsy to examine the villus morphology, by biochemical assessment of nutrient absorption, by patient weight gain, or by amelioration of the symptoms associated with these conditions. Other conditions that may be treated by the subject method, or for which the subject method may be useful prophylactically, include radiation enteritis, infectious or post-infectious enteritis, regional enteritis (Crohn's disease), small intestinal damage due to toxic or other chemotherapeutic agents, and patients with short bowel syndrome.

More generally, the present invention provides a therapeutic method for treating digestive tract diseases. The term "digestive tract" as used herein means a tube through which food passes, including stomach and intestine. The term "digestive tract diseases" as used herein means diseases accompanied by a qualitative or quantitative abnormality in the digestive tract mucosa, which include, e. g., ulceric or inflammatory disease; congenital or acquired digestion and absorption disorder including malabsorption syndrome; disease caused by loss of a mucosal barrier function of the gut; and protein-losing gastroenteropathy. The ulceric disease includes, e.g., gastric ulcer, duodenal ulcer, small intestinal ulcer, colonic ulcer and rectal ulcer. The inflammatory disease include, e.g., esophagitis, gastritis, duodenitis, enteritis, colitis, Crohn's disease, proctitis, gastrointestinal Behcet, radiation enteritis, radiation colitis, radiation proctitis, enteritis and medicamentosa. The malabsorption syndrome includes the essential malabsorption syndrome such as disaccharide-decomposing enzyme deficiency, glucose-galactose malabsorption, fructose malabsorption; secondary malabsorption syndrome, e.g., the disorder caused by a mucosal atrophy in the digestive tract through the intravenous or parenteral nutrition or elemental diet, the disease caused by the resection and shunt of the small intestine such as short gut syndrome, cul-de-sac syndrome; and indigestible malabsorption syndrome such as the disease caused by resection of the stomach, e.g., dumping syndrome.

The term "therapeutic agent for digestive tract diseases" as used herein means the agents for the prevention and treatment of the digestive tract diseases, which include, e.g., the therapeutic agent for digestive tract ulcer, the therapeutic agent for inflammatory digestive tract disease, the therapeutic agent for mucosal atrophy in the digestive tract and the therapeutic agent for digestive tract wound, the amelioration agent for the function of the digestive tract including the agent for recovery of the mucosal barrier function and the amelioration agent for digestive and absorptive function. The ulcers include digestive ulcers and erosions, acute ulcers, namely, acute mucosal lesions.

The subject method, because of promoting proliferation of intestinal mucosa, can be used in the treatment and prevention of pathologic conditions of insufficiency in digestion and absorption, that is, treatment and prevention of mucosal atrophy, or treatment of hypoplasia of the digestive tract tissues and decrease in these tissues by surgical removal as well as improvement of digestion and absorption. Further, the subject method can be used in the treatment of pathologic mucosal conditions due to inflammatory diseases such as enteritis, Crohn's disease and ulceric colitis and also in the treatment of reduction in function of the digestive tract after operation, for example, in damping syndrome as well as in the treatment of duodenal ulcer in conjunction with the inhibition of peristalsis of the stomach and rapid migration of food from the stomach to the jejunum. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

Likewise, the DPIV inhibitors of the subject invention can be used to alter the plasma half-life of secretin, VIP, PHI, PACAP, GIP and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

Neuropeptide Y (NPY) is believed to act in the regulation vascular smooth muscle tone, as well as regulation of blood pressure. NPY also decreases cardiac contractility. NPY is also the most powerful appetite stimulant known (Wilding et al., (1992) *J Endocrinology* 132:299-302). The centrally evoked food intake (appetite stimulation) effect is predominantly mediated by NPY Y1 receptors and causes increase in body fat stores and obesity (Stanley et al., (1989) *Physiology and Behavior* 46:173-177).

According to the present invention, a method for treatment of anorexia comprises administering to a host subject an effective amount of a DPIV inhibitor to stimulate the appetite and increase body fat stores which thereby substantially relieves the symptoms of anorexia.

A method for treatment of hypotension comprises administering to a host subject an effective amount of a DPIV inhibitor of the present invention to mediate vasoconstriction and increase blood pressure which thereby substantially relieves the symptoms of hypotension.

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) *Peptide Res* 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

C. Examples of Peptidyl DPIV Inhibitors

In the case of DPIV inhibitors, a preferred class of inhibitors are peptidyl compounds based on the dipeptides Pro-Pro or Ala-Pro. Another preferred class of peptidyl inhibitors are compounds based on the dipeptide (D)-Ala-(L)-Ala. In many embodiments, it will be desirable to provide the peptidyl moiety as a peptidomimetic, e.g., to increase bioavailability and/or increase the serum half-life relative to the equivalent peptide. For instance, a variety of peptide backbone analogs are available in the art and be readily adpated for use in the subject methods.

In an exemplary embodiment, the peptidomimetic can be derived as a retro-inverso analog of the peptide. To illustrate, certain of the subject peptides can be generated as the retro-inverso analog (shown in its unprotected state):

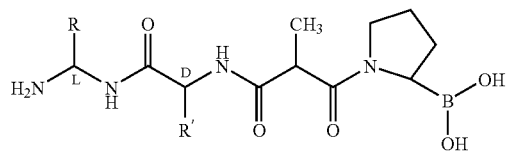

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the N-terminal amino acid analogs is synthesized by treating an N-Boc-protected amino acid (having the sidechain R) with ammonia under HOBT-DCC coupling conditions to yield amide, and then effecting a Hofmann-type rearrangement with I,I-bis-(trifluoroacetoxy) iodobenzene (TIB), as described in Radhakrishna et al. (1979) *J. Org. Chem.* 44:1746. The product amine salt is then coupled to a side-chain protected (e.g., as the benzyl ester) N-Fmoc D-enatiomer of the second amino acid residue (e.g., having a sidechain R') under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog. The pseudotripeptide is then coupled with (protected) boro-proline under standard conditions to give the protected tetrapeptide analog. The protecting groups are removed to release the final product, which is purified by HPLC.

In another illustrative embodiment, the peptidomimetic can be derived as a retro-enantio analog of the peptide.

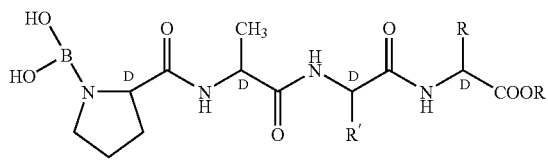

Retro-enantio analogs such as this can be synthesized using D-enatiomers of commercially available D-amino acids or other amino acid analogs and standard solid- or solution-phase peptide-synthesis techniques.

In still another illustrative embodiment, trans-olefin derivatives can be made with the subject boronophenylalanine analogs. For example, an exemplary olefin analog is:

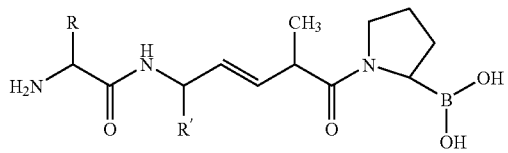

The trans olefin analog can be synthesized according to the method of Y. K. Shue et al. (1987) Tetrahedron Letters 28:3225.

Still another class of peptidomimetic boronophenylalanine derivatives include the phosphonate derivatives, such as:

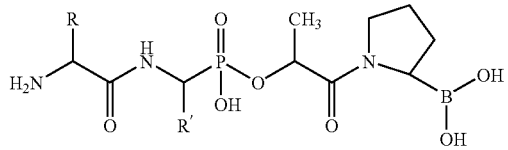

The synthesis of such phosphonate derivatives can be adapted from known synthesis schemes. See, for example, Loots et al. in Peptides: Chemistry and Biology, (Escom Science Publishers, Leiden, 1988, p. 118); Petrillo et al. in Peptides: Structure and Function (Proceedings of the 9th American Peptide Symposium, Pierce Chemical Co. Rockland, Ill., 1985).

D. Non-peptidyl DPIV Inhibitors

The pharmaceutical industry has developed a variety of different strategies for assessing millions of compounds a year as potential lead compounds based on inhibitory activity against an enzyme. DPIV and other proteolytic enzymes targeted by the subject method are amenable to the types of high throughput screening required to sample large arrays of compounds and natural extracts for suitable inhibitors.

As an illustrative embodiment, the ability of a test agent to inhibit DPIV can be assessed using a calorimetric or fluorometric substrate, such as Ala-Pro-paranitroanilide. See U.S. Pat. No. 5,462,928. Moreover, DPIV can be purified, and is accordingly readily amenable for use in such high throughput formats as multi-well plates.

Briefly, DPIV is purified from pig kidney cortex (Barth et al. (1974) Acta Biol Med Germ 32:157; Wolf et al. (1972) Acta Bio Mes Germ 37:409) or human placenta (Puschel et al. (1982) Eur J Biochem 126:359). An illustrative reaction mixture includes 50 µM sodium Hepes (pH7.8), 10 µM Ala-Pro-paranitroanilide, 6 milliunits of DPIV, and 2% (v/v) dimethylformamide in a total volume of 1.0 mL. The reaction is initiated by addition of enzyme, and formation of reaction product (paranitroanilide) in the presence and absence of a test compound can be detected photometrically, e.g., at 410 nm.

Exemplary compounds which can be screened for activity against DPIV (or other relevant enzymes) include peptides, nucleic acids, carbohydrates, small organic molecules, and natural product extract libraries, such as isolated from animals, plants, fungus and/or microbes.

E. Assays of Insulinotropic Activity

In selecting a compound suitable for use in the subject method, it is noted that the insulinotropic property of a compound may be determined by providing that compound to animal cells, or injecting that compound into animals and monitoring the release of immunoreactive insulin (IRI) into the media or circulatory system of the animal, respectively. The presence of IRI can be detected through the use of a radioimmunoassay which can specifically detect insulin.

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). The db/db mice can purchased from, for example, The Jackson Laboratories (Bar Harbor, Me.). In an exemplary embodiment, for treatment of the mice with a regimen including a DPIV inhibitor or control, sub-orbital sinus blood samples are taken before and at some time (e.g., 60 minutes) after dosing of each animal. Blood glucose measurements can be made by any of several conventional techniques, such as using a glucose meter. The blood glucose levels of the control and DPIV inhibitor dosed animals are compared The metabolic fate of exogenous GLP-1 can also be followed in either nondiabetic and type II diabetic subjects, and the effect of a candidate DPIV inhibitor determined. For instance, a combination of high-pressure liquid chromatography (HPLC), specific radioimmunoassays (RIAs), and a enzyme-linked immunosorbent assay (ELISA), can be used, whereby intact biologically active GLP-1 and its metabolites can be detected. See, for example, Deacon et al. (1995) Diabetes 44:1126-1131. To illustrate, after GLP-1 administration, the intact peptide can be measured using an NH2-terminally directed RIA or ELISA, while the difference in concentration between these assays and a COOH-terminal-specific RIA allowed determination of NH2-terminally truncated metabolites. Without inhibitor, subcutaneous GLP-1 is rapidly degraded in a time-dependent manner, forming a metabolite which co-elutes on HPLC with GLP-I(9-36) amide and has the same immunoreactive profile. For instance, thirty minutes after subcutaneous GLP-1 administration to diabetic patients (n=8), the metabolite accounted for 88.5+ 1.9% of the increase in plasma immunoreactivity determined by the COOH-terminal RIA, which was higher than the levels measured in healthy subjects (78.4+3.2%; n=8; P<0.05). See Deacon et al., supra. Intravenously infused GLP-1 was also extensively degraded.

F. Pharmaceutical Formulations

The inhibitors can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agenit, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

Glucose metabolism can be altered, and symptoms associated with type II diabetes can be decreased or eliminated, in accordance with a "timed" administration of DPIV inhibitors wherein one or more appropriate indices for glucose metabolism and/or type II diabetes can be used to assess effectiveness of the treatment (dosage and/or timing): e.g. glucose tolerance, glucose level, insulin level, insulin sensitivity, glycosylated hemoglobin.

An effective time for administering DPIV inhibitors needs to be identified. This can be accomplished by routine experiment as described below, using one or more groups of animals (preferably at least 5 animals per group).

In animals, insulinotropic activity by DPIV inhibitor treatment can be assessed by administering the inhibitor at a particular time of day and measuring the effect of the administration (if any) by measuring one or more indices associated with glucose metabolism, and comparing the post-treatment values of these indices to the values of the same indices prior to treatment.

The precise time of administration and/or amount of DPIV inhibitor that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

While the subject is being treated, glucose metabolism is monitored by measuring one or more of the relevant indices at predetermined times during a 24-hour period. Treatment (amounts, times of administration and type of medication) may be adjusted (optimized) according to the results of such monitoring. The patient is periodically reevaluated to determine extent of improvement by measuring the same parameters, the first such reevaluation typically occurring at the end of four weeks from the onset of therapy, and subsequent reevaluations occurring every 4 to 8 weeks during therapy and then every 3 months thereafter. Therapy may continue for several months or even years with six months being a typical length of therapy for humans.

Adjustments to the amount(s) of drug(s) administered and possibly to the time of administration may be made based on these reevaluations. For example, if after 4 weeks of treatment one of the metabolic indices has not improved but at least one other one has, the dose could be increased by ⅓ without changing the time of administration.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

The phrase "therapeutically-effective amount" as used herein means that amount of, e.g., a DPIV inhibitor(s), which is effective for producing some desired therapeutic effect by inhibiting, for example, ittie proteolysis of a peptide hormone at a reasonable benefit/risk ratio applicable to any medical treatment.

The phrase "pharmaceutically acceptable" is employed herein to refer to those DPIV inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid, (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of DPIV inhibitors. These salts can be prepared in situ during the final isolation and purification of the DPIV Inhibitors, or by separately reacting a purified DPIV inhibitor in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the DPIV inhibitor useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a DPIV inhibitor(s). These salts can likewise be prepared in situ during the final isolation and purification of the DPIV inhibitor(s), or by separately reacting the purified DPIV inhibitor(s) in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin; propyl gallate, alpha-tocopherol, and the like; and (3) metal chelating agents, such as citric acid, ethylenediamine tetraacetic acid (EDTA), sorbitol tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a DPIV inhibitor(s) with the carrier and, optionally, one or more accessory ingredients. In general, the formulations are prepared by uniformly and intimately bringing into association a DPIV inhibitor with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a DPIV inhibitor(s) as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols,. sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydrbxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active DPIV inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more DPIV inhibitor(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a DPIV inhibitor(s) include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to DPIV inhibitor(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a DPIV inhibitor(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The DPIV inhibitor(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a DPIV inhibitor(s) to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more DPIV inhibitor(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying. agents and dispersing agents. Prevention of the. action of microorganisms may be ensured by the inclusion of various antibacterial and antifungal agents, for example, paraben, chlorobutanol, phenol sorbic acid, and the like. It may also be desirable to include isotonic agents, such as sugars; sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of DPIV inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the DPIV inhibitor(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid; intraspinal and intrasternal injection and infusion.

The phrases "systemic administration," "administered systemically," "peripheral administration" and "administered peripherally" as used herein mean the administration of a DPIV inhibitor, drug or other material other than directly into the central nervous system, such that it enters the patient's system and, thus, is subject to metabolism and other like processes, for example, subcutaneous administration.

These DPIV inhibitor(s) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the DPIV inhibitor(s), which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

G. Conjoint Administration

Another aspect of the invention provides a conjoint therapy wherein one or more other therapeutic agents are administered with the protease inhibitor. Such conjoint treatment may be achieved by way-of the simultaneous, sequential or separate dosing of the individual components of the treatment.

In one embodiment, a DPIV inhibitor is conjointly administered with insulin or other insulinotropic agents, such as GLP-1 or a gene therapy vector which causes the ectopic expression of GLP-1.

In another illustrative embodiment, the subject inhibitors can be conjointly administered with a an M1 receptor antagonist. Cholinergic agents are potent modulators of insulin release that act via muscarinic receptors. Moreover, the use of such agents can have the added benefit of decreasing cholesterol levels, while increasing HDL levels. Suitable muscarinic receptor antagonists include substances that directly or indirectly block activation of muscarinic cholinergic receptors. Preferably, such substances are selective (or are used in amounts that promote such selectivity) for the M1 receptor. Nonlimiting examples include quaternary. amines (such as methantheline, ipratropium, and propantheline), tertiary amines (e.g. dicyclomine, scopolamine) and tricyclic amines (e.g. telenzepine). Pirenzepine and methyl scopolamine are preferred. Other suitable muscarinic receptor antagonists include benztropine (commercially available as COGENTIN from Merck), hexahydro-sila-difenidol hydrochloride (HHSID hydrochloride disclosed in Lambrecht et al. (1989) Trends in Pharmacol. Sci. 10(Suppl): 60; (+/−)-3-quinuclidinyl xanthene-9-carboxylate hemioxalate (QNX-hemioxalate; Birdsall et al., Trends in Pharmacol. Sci. 4:459, 1983; telenzepine dihydrochloride (Coruzzi et al. (1989) Arch. Int. Pharmacodyn. Ther. 302:232; and Kawashima et al. (1990) Gen. Pharmacol. 21:17) and atropine. The dosages of such muscarinic receptor antagonists will be generally subject to optimization as outlined above. In the case of lipid metabolism disorders, dosage optimization may be necessary independently of whether administration is timed by reference to the lipid metabolism responsiveness window or not.

In terms of regulating insulin and lipid metabolism and reducing the foregoing disorders, the subject DPIV inhibitors may also act synergistically with prolactin inhibitors such as d2 dopamine agonists (e.g. bromocriptine). Accordingly, the subject method can include the conjoint administration of such prolactin inhibitors as prolactin-inhibiting ergo alkaloids and prolactin-inhibiting dopamine agonists. Examples of suitable compounds include 2-bromo-alpha-ergocriptine, 6-methyl-8 beta-carbobenzyloxyaminoethyl-10-alpha-ergoline, 8-acylaminoergolines, 6-methyl-8-alpha-(N-acyl) amino-9-ergoline, 6-methyl-8-alpha-(N-phenylacetyl) amino-9-ergoline, ergocomine, 9,10-dihydroergocornine, D-2-halo-6-alkyl-8-substituted ergolines, D-2-bromo-6-methyl-8-cyanomethylergoline, carbidopa, benserazide and other dopadecaiboxylase inhibitors, L-dopa, dopamine and non toxic salts thereof.

The DPIV inhibitors used according to the invention can also be used conjointly. with agents acting on the ATP-dependent potassium channel of the β-cells, such as glibenclamide, glipizide, gliclazide and AG-EE 623 ZW. The DPIV inhibitors may also advantageously be applied in combination with other oral agents such as metformin and related compounds or glucosidase inhibitors as, for example, acarbose.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis of BoroProline

Referring to FIG. 1, the starting compound I is prepared essentially by the procedure of Matteson et al. (Organometallics 3:1284, 1984), except that a pinacol ester is substituted for the pinanediol ester. Similar compounds such as boropipecolic acid and 2-azetodine boronic acid can be prepared by making the appropriate selection of starting material to yield the pentyl and propyl analogs of compound I. Further, Cl can be substituted for Br in the formula, and other diol protecting groups can be substituted for pinacol in the formula, e.g., 2,3-butanediol and alphapinanediol.

Compound II is prepared by reacting compound I with [(CH$_3$)O$_3$Si]$_2$N—Li$^+$. In this reaction hexamethyldisilazane is dissolved in tetrahydrofuran and an equivalent of n-butyllithium added at −78° C. After warming to room temperature (20° C.) and cooling to −78° C., an equivalent of compound I is added in tetrahydrofuran. The mixture is allowed to slowly come to room temperature and to stir overnight. The alpha-bis[trimethylsilane]-protected amine is isolated by evaporating solvent and adding hexane under anhydrous conditions. Insoluble residue is removed by filtration under a nitrogen blanket, yielding a hexane solution of compound II.

Compound III, the N-trimethysilyl protected form of boroProline is obtained by the thermal cyclization of compound II during the distillation process in which compound II is heated to 100-150° C. and distillate is collected which boils 66-62° C. at 0.06-0.10 mm pressure.

Compound IV, boroProline-pinacol hydrogen chloride, is obtained by treatment of compound III with HCl:dioxane.

Excess HCl and by-products are removed by trituration with ether. The final product is obtained in a high degree of purity by recrystallization from ethyl acetate.

The boroProline esters can also be obtained by treatment of the reaction mixture obtained in the preparation of compound II with anhydrous acid to yield 1-amino-4-bromobutyl boronate pinacol as a salt. Cyclization occurs after neutralizing the salt with base and heating the reaction.

Example 2

Preparation of boroProline-pinacol

The intermediate, 4-Bromo-1-chlorobutyl boronate pinacol, was prepared by the method in Matteson et al. (Organometallics 3:1284, 1984). except that conditions were modified for large scale preparations and pinacol was substituted for the pinanediol protecting group.

3-bromopropyl boronate pinacbl was prepared by hydrogenboronation of allyl bromide (173 ml, 2.00 moles) with catechol borane (240 ml, 2.00 moles). Catechol borane was added to allyl bromide and the reaction heated for 4 hours at 100° C. under a nitrogen atmosphere. The product, 3-bromoprdpyl boronate catechol (bp 95-102° C., 0.25 mm), was isolated in a yield of 49% by distillation. The catechol ester (124 g, 0.52 moles) was transesterified with pinacol (61.5 g, 0.52 moles) by mixing the component in 50 ml of THF and allowing them to stir for 0.5 hours at 0° C. and 0.5 hours at room temperature. Solvent was removed by evaporation and 250 ml of hexane added. Catechol was removed as a crystalline solid. Quantitative removal was achieved by successive dilution to 500 ml and to 1000 ml with hexane and removing crystals at each dilution. Hexane was evaporated and the product distilled to yield 177 g (bp 60-64° C., 0.35 mm).

4-Bromo-1-chlorobutyl boronate pinacol was prepared by homologation of the corresponding propyl boronate. Methylene chloride (50.54 ml, 0.713 moles) was dissolved in 500 ml of THF, 1.54N n-butyllithium in hexane (480 ml, 0.780 moles) was slowly added at −100° C. 3-Bromopropyl boronate pinacol (178 g, 0.713 moles) was dissolved in 500 ml of THG, cooled to the freezing point of the solution, and added to the reaction mixture. Zinc chloride (54.4 g, 0.392 moles) was dissolved in 250 ml of THG, cooled to 0° C., and added to the reaction mixture in several portions. The reaction was allowed to slowly warm to room temperature and to stir overnight. Solvent was evaporated and the residue dissolved in hexane (1 liter) and washed with water (1 liter). Insoluble material was discarded. After drying over anhydrous magnesium sulfate and filtering, solvent was evaporated. The product was distilled to yield 147 g (bp 110-112° C., 0.200 mm).

N-Trimethylsilyl-boroProline pinacol was prepared first by dissolving hexamethyldisilizane (20.0 g, 80.0 mmoles) in 30 ml of THF, cooling the solution to −78° C., and adding 1.62N n-butyllithium in hexane (49.4 ml, 80.0 mmoles). The solution was allowed to slowly warm to room temperature. It was recooled to −78° C. and 4-bromo-1-chlorobutyl boronate pinacol (23.9 g, 80.0 mmoles) added in 20 ml of THF. The mixture was allowed to slowly warm to room temperature and to stir overnight. Solvent was removed by evaporation and dry hexane (400 ml) added to yield a precipitant which was removed by filbration under a nitrogen atmosphere. The filtrate was evaporated and the residue distilled, yielding 19.4 g of the desired product (bp 60-62° C., 0.1-0.06 mm).

H-boroProline-pinacol.HCl (boroProline-pinacol.HCl) was prepared by cooling N-trimethylsilyl-boroProline pinacol (16.0 g, 61.7 mmoles) to −78° C. and adding 4N HCL: dioxane 46 ml, 185 mmoles). The mixture was stirred 30 minutes at −78° C. and 1 hour at room temperature. Solvent was evaporated and the residue triturated with ether to yield a solid. The crude product was dissolved in chloroform and insoluble material removed by filtration. The solution was evaporated and the product crystallized from ethyl acetate to yield 11.1 g of the desired product (mp 156.5-157° C.).

Example 3

Synthesis of BoroProline Peptides

General methods of coupling of N-protected peptides and amino acids with suitable side-chain protecting groups to H-boroProline-pinacol are applicable. When needed, side-chain protecting and N-terminal protecting groups can be removed by treatment with anhydrous HCl, HBr, trifluoroacetic acid, or by catalytic hydrogenation. These procedures are known to those skilled in the art of peptide synthesis.

The mixed anhydride procedure of Anderson et al. (J. Am. Chem. Soc. 89:5012, 1984) is preferred for peptide coupling. Referring again to FIG. 1, the mixed anhydride of an N-protected amino acid or a peptide is prepared by dissolving the peptide in tetrahydrofuran and adding one equivalent of N-methylmorpholine. The solution is cooled to −20° C. and an equivalent of isobutyl chloroformate is added. After 5 minutes, this mixture and one equivalent of triethylamine (or other sterically hindered base) are added to a solution of H-boroPro-pinacol dissolved in either cold chloroform of tetrahydrofuran.

The reaction mixture is routinely stirred for one hour at −20° C. and 1 to 2 hours at room temperature (20° C.). Solvent is removed by evaporation, and the residue is dissolved in ethyl acetate. The organic solution is washed with 0.20N hydrochloric acid, 5% aqueous sodium bicarbonate, and saturated aqueous sodium chloride. The organic phase is dried over anhydrous sodium sulfate, filtered, and evaporated. Products are purified by either silica gel chromatography or gel permeation chromatography using Sephadex TM LH-20 and methanol as a solvent.

Previous studies have shown that the pinacol protecting group can be removed in situ by preincubation in phosphate buffer prior to running biological experiments (Kettner et al., J. Biol. Chem. 259:15106, 1984). Several other methods are also applicable for removing pinacol groups from peptides, including boroProline, and characterizing the final product. First, the peptide can be treated with diethanolamine to yield the corresponding diethanolamine boronic acid ester, which can be readily hydrolyzed by treatment with aqueous acid or a sulfonic acid substituted polystyrene resin as described in Kettner et al. (supra). Both pinacol and pinanediol protecting groups can be removed by treating with BC13 in methylene chloride as described by Kinder et al. (J. Med. Chem. 28:1917). Finally, the free boronic acid can be converted to the difluoroboron derivative (-BF2) by treatment with aqueous HF as described by Kinder et al. (supra).

Similarly, different ester groups can be introduced by reacting the free boronic acid with various di-hydroxy compounds (for example, those containing heteroatoms such as S or N) in an inert solvent.

Example 4

Preparation of H-Ala-boroPro

Boc-Ala-boroPro was prepared by mixed anhydride coupling of the N-Boc-protected alanine and H-boroPro prepared as described above. H-Ala-boroPro (Ala-boroPro) was prepared by removal of the Boc protecting group at 0° C. in 3.5 molar excess of 4N HCl-dioxane. The coupling and deblocking reactions were performed by standard chemical reaction. Ala-boroPro has a $K_i$ for DP-IV of in the nanomolar range. Boc-blocked Ala-boroPro has no affinity for DP-IV.

The two diastereomers of Ala-boroPro-pinacol, L-Ala-D-boroPro-pinacol and L-Ala-L-boroPro-pinacol, can be partially separated by silica gel chromatography with 20% methanol in ethyl acetate as eluant. The early fraction appears by NMR analysis to be 95% enriched in one isomer. Because this fraction has more inhibits DP-IV to a greater extent than later fractions (at equal concentrations) it is probably enriched in the L-boroPro (L-Ala-L-boroPro-pinacol) isomer.

Example 5

Glucose Tolerance Test

Figure 2:
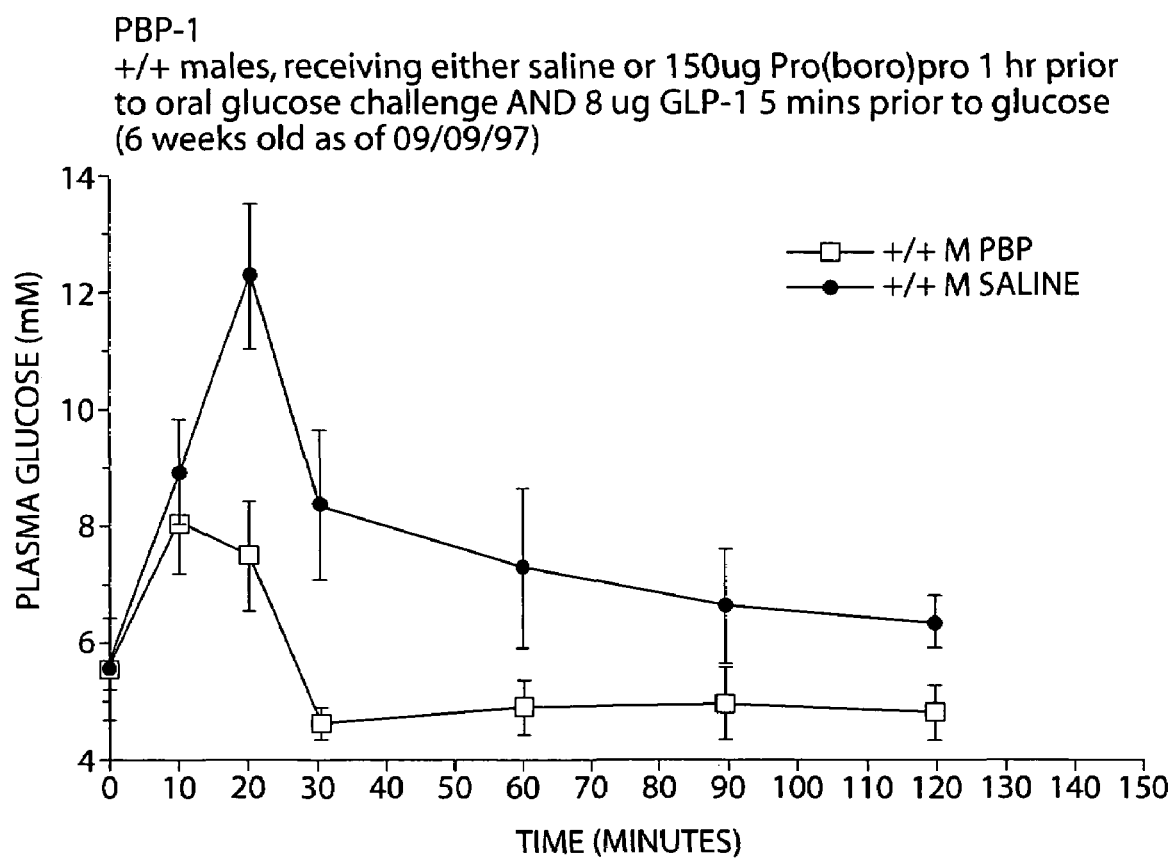
FIG. 2 is a glucose tolerance curve which shows that a single injection of PBP-1 improves glucose levels in blood; The glucose concentration is measured before and at 30-minute intervals after the test dose of glucose. This figure demonstrates that a single injection of PBP-1 potentiates the response to a sub-therapeutic dose of GLP-1.
Figure 3:
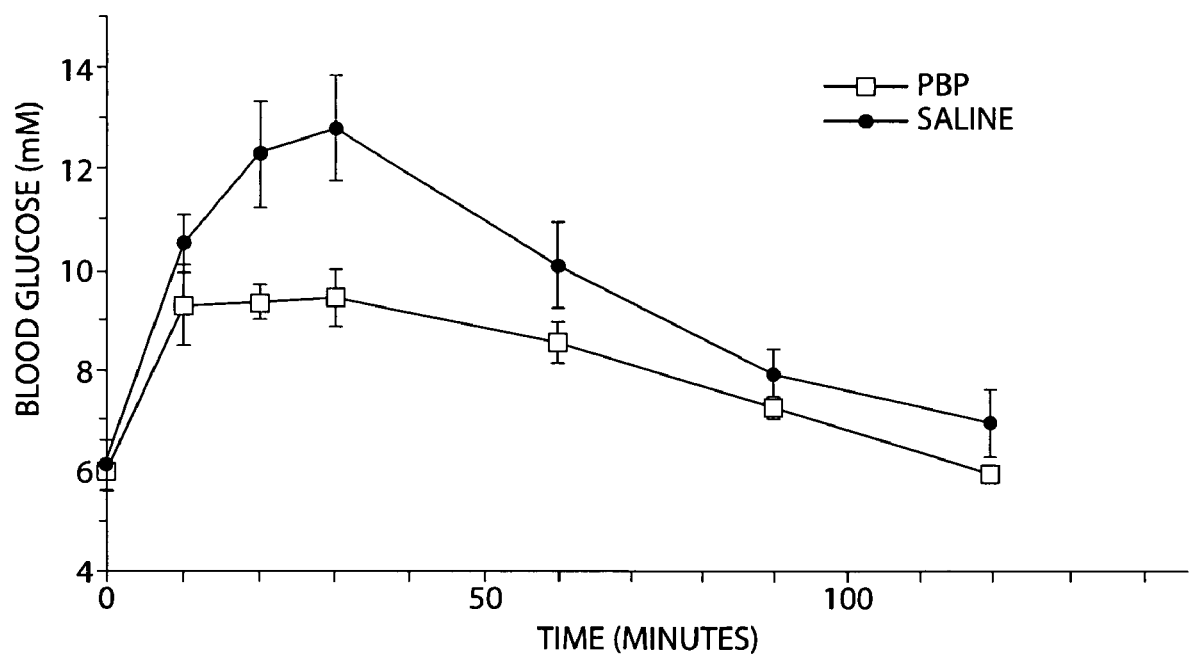
FIG. 3 shows that a single injection of PBP-2 improves glucose levels in blood.

Experiments show that Pro-boro-pro clearly lowers blood sugar based upon results from an oral glucose challenge in mice. The first two experiments are "acute" experiments wherein the mice were injected with a single dose of Pro-boro-pro. In the first set of experiments mice were injected with 150 μg of Pro-boro-pro (PBP-1) and then subjected to an oral glucose tolerance test within an hour. 8 μg of GLP-1 was also administered to these mice five minutes prior to administration of glucose. See FIG. 2. In a second set of experiments mice were injected with Pro-boro-pro (PBP-2) one hour prior to an oral glucose challenge test. FIG. 3 presents the results of these experiments. Each set of experiments was also performed using saline as a control.

Figure 4:
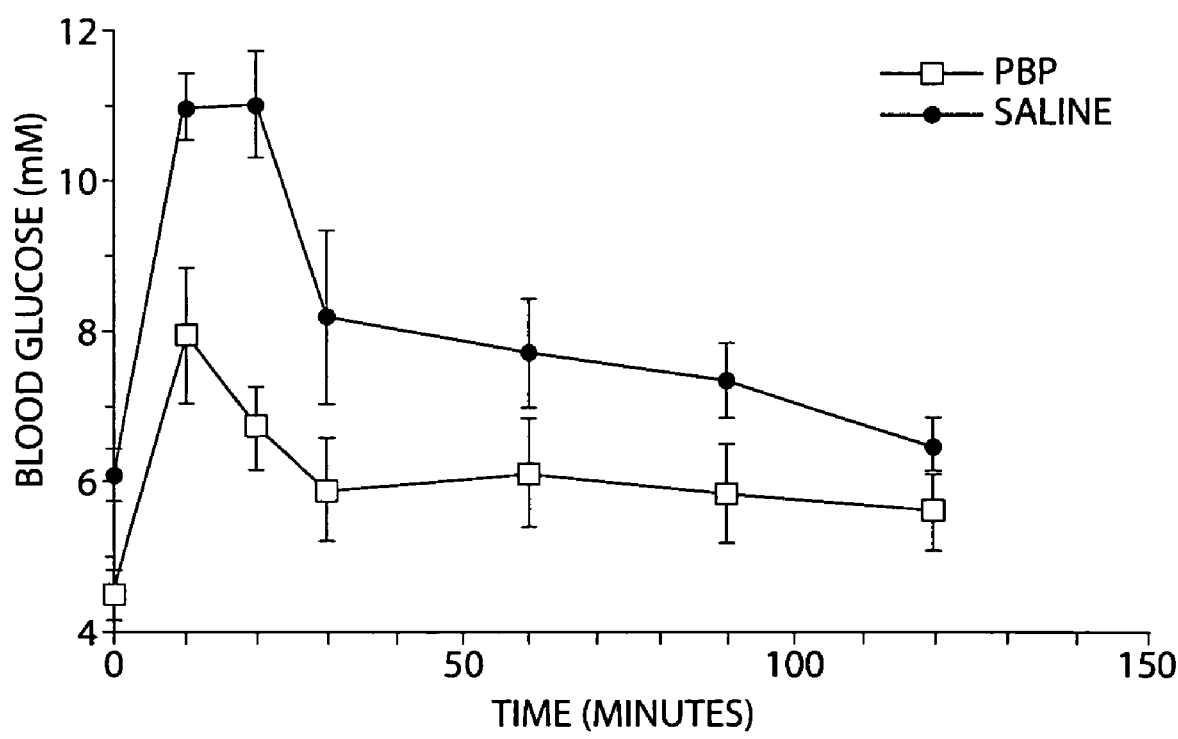
FIG. 4 shows that treatment with PBP-3 under "chronic" conditions also results in lowering of the blood sugar levels.
Figure 5A:
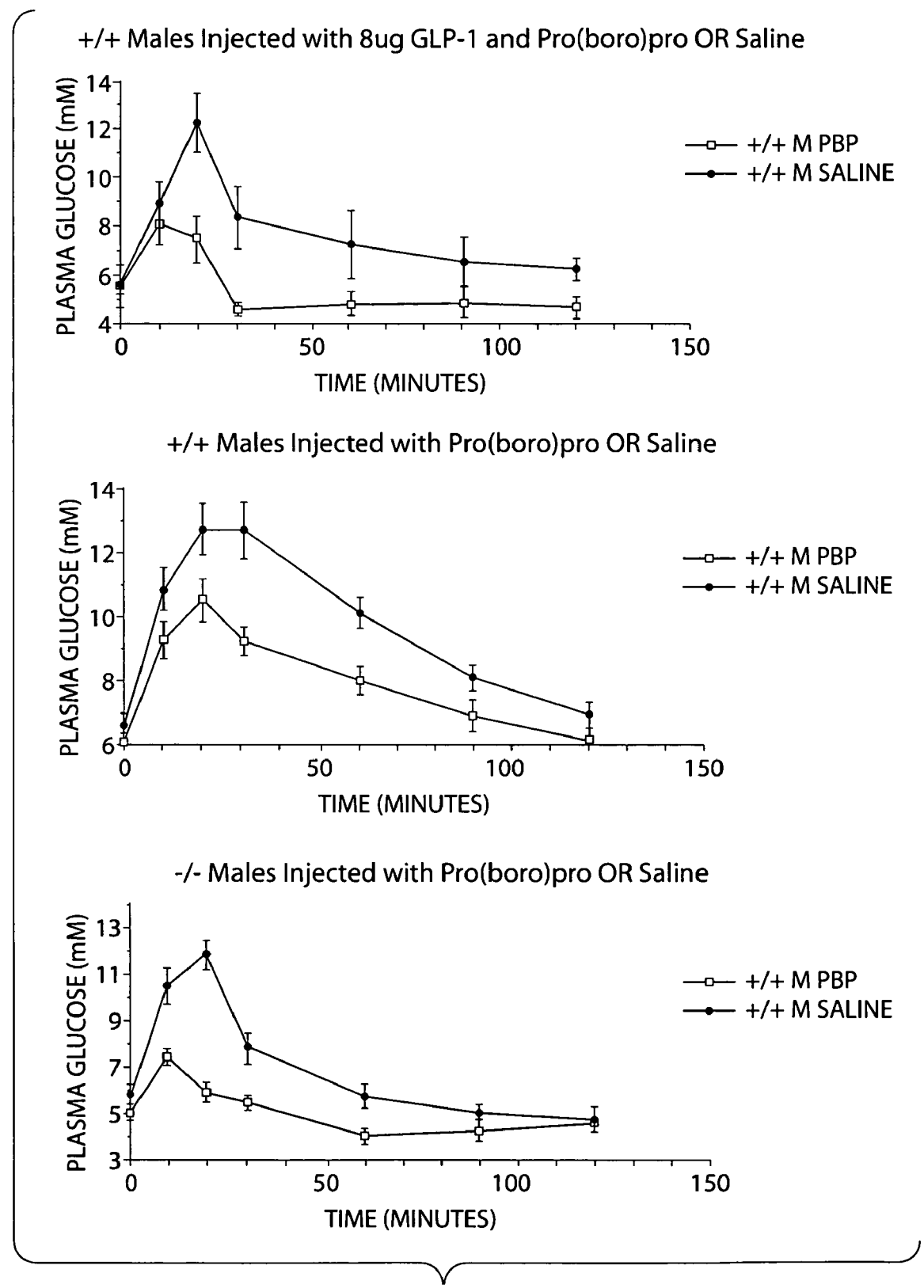
FIGS. 5A and 5B compare the ability of Pro-boro-pro to lower plasma glucose levels in GLP-1 receptor -/- transgenic mice.
Figure 5B:
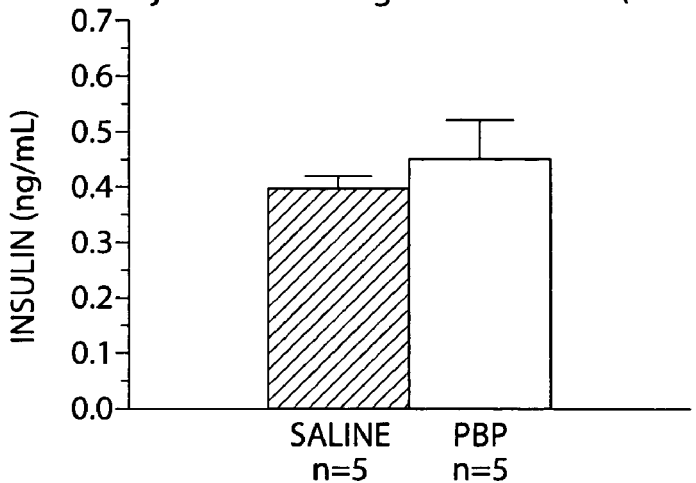
Figure 5B:
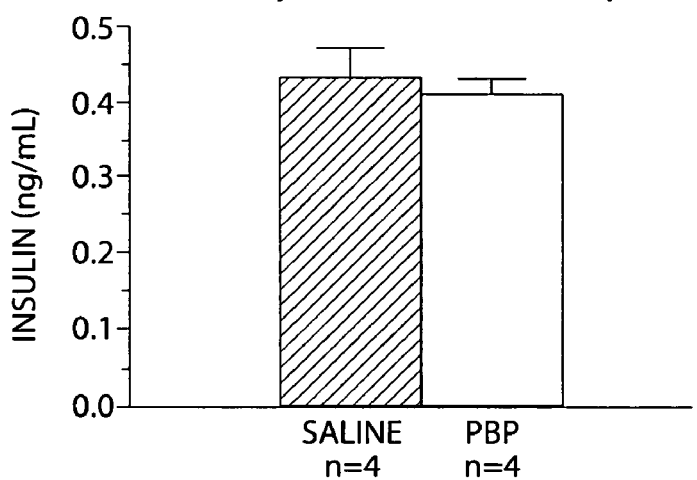
Figure 5B:
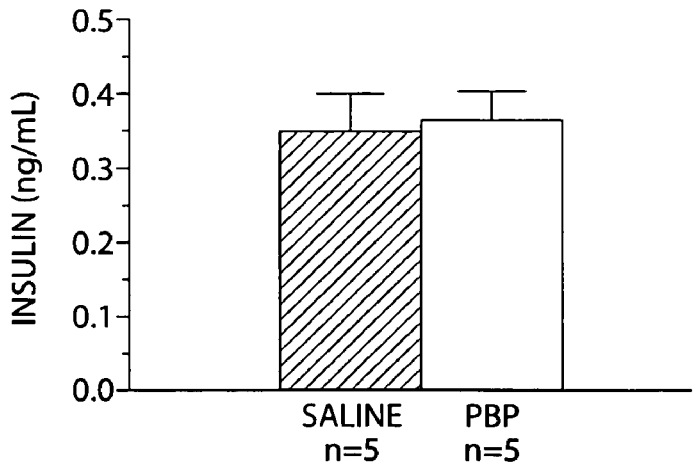

The third set of experiments were "chronic" experiments, wherein the mice were injected twice daily with Pro-boro-pro for-four days, followed by an oral glucose challenge. These results are presented in FIG. 4.

Example 6

Glizcose Tolerance Test, Comparison of Normal and GLP-1 Receptor -/- Mice

GLP-1 receptor gene "knock-out" causes glucose intolerance in transgenic mice. Gallwitz B; Schmidt WE Z Gastroenterol (1997) 35: 655-8. FIG. 5 compares the ability of Pro-boro-pro to lower plasma glucose levels in normal and GLP-1 receptor -/- transgenic mice.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for treating Type II diabetes in an animal, comprising conjointly administering to the animal metformin and an inhibitor of dipeptidylpeptidase IV or a pharmaceutically acceptable salt thereof in an amount sufficient to treat Type II diabetes, wherein the amount of said inhibitor of dipeptidylpeptidase IV or pharmaceutically acceptable salt thereof is not sufficient to suppress the immune system of the animal.

2. The method of claim 1, wherein the inhibitor reduces insulin resistance, glucose intolerance, hyperglycemia, or hyperinsulinemia.

3. The method of claim 1, wherein the inhibitor has an $EC_{50}$ for modification of glucose metabolism which is at least one order of magnitude less than its $EC_{50}$ for immunosuppression.

4. The method of claim 1, wherein the inhibitor has a $K_i$ for dipeptidylpeptidase IV inhibition of 10 nM or less.

5. The method of claim 1, wherein the inhibitor has a $K_i$ for dipeptidylpeptidase IV inhibition of 1.0 nM or less.

6. The method of claim 1, wherein the inhibitor has a molecular weight less than 7500 amu.

7. The method of claim 1, wherein the inhibitor is administered orally.

8. The method of claim 1, wherein the inhibitor is a peptidomimetic of a peptide selected from the group consisting of Pro-Pro, Ala-Pro, and (D)-Ala-(L)-Ala.

9. The method of claim 1, wherein the inhibitor is represented by Formula I:

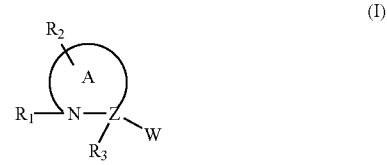

wherein,
A represents a 4-8 membered heterocycle including a N and a Cα carbon;
Z represents C or N;
W represents CN, —CH=NR$_5$,

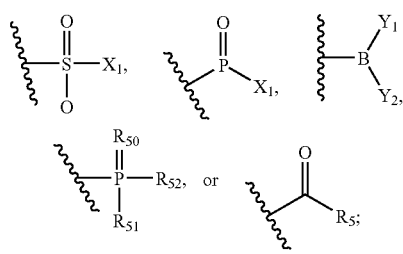

R$_1$ represents a C-terminally linked amino acid residue, a C-terminally linked amino acid analog, a C-terminally linked peptide, a C-terminally linked peptide analog, an amino-protecting group

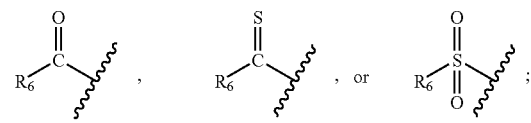

R$_2$ is absent or represents one or more substitutions to the ring A, each of which can independently be a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —(CH$_2$)$_m$—R$_7$, —(CH$_2$)$_m$OH, —(CH$_2$)$_m$—O-lower alkyl, —(CH$_2$)$_m$—O-lower alkenyl, —(CH$_2$)$_n$—

O—(CH$_2$)$_m$—R$_7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$_7$;

if Z is N, R$_3$ represents a hydrogen;

if Z is C, R$_3$ represents a hydrogen, a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —(CH$_2$)$_m$—R$_7$, —(CH$_2$)$_m$—OH, —(CH$_{2m}$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$_7$;

R$_5$ represents a hydrogen, an alkyl, an alkenyl, an alkynyl, —C(X$_1$)(X$_2$)X$_3$, —(CH$_2$)$_m$—R$_7$, —(CH$_2$)$_n$—OH, —(CH$_2$)$_n$—O-alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-alkyl, —(CH$_2$)$_n$—S-alkenyl, —(CH$_2$)$_n$—S-alkynyl, —(CH$_2$)$_n$—S—(CH$_2$)$_m$—R$_7$, —C(O)C(O)NH$_2$, or —C(O)C(O)OR'$_7$, R$_6$ represents a hydrogen, a halogen, an alkyl, an alkenyl, an alkynyl, an aryl, —(CH$_2$)$_m$R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$S-alkynyl, —(CH$_2$)$_m$—S—(CH$_2$)$_m$—R$_7$,

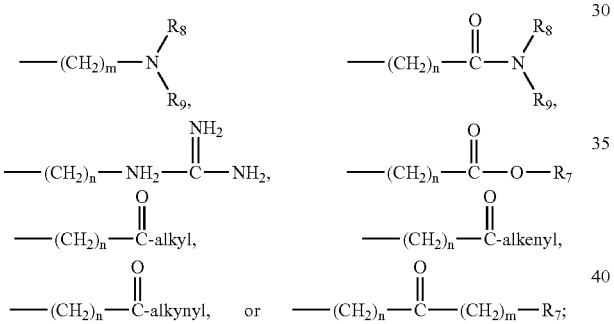

R$_7$ represents, for each occurrence, a substituted or unsubstituted aryl, aralkyl, cycloalkyl, cycloalkenyl or heterocyclyl;

R'$_7$ represents, for each occurrence, hydrogen, a substituted or unsubstituted alkyl, alkenyl, aryl, aralkyl, cycloalkyl, cycloalkenyl or heterocyclyl;

R$_8$ and R$_9$ each independently represent hydrogen, alkyl, alkenyl, —(CH$_2$)$_m$—R$_7$, —C(=O)-alikyl, —C(=O)-alkenyl, —C(=O)-alkynyl, or —C(=O)—(CH$_2$)$_m$—R$_7$, or R$_8$ and R$_9$ taken together with the N atom to which they are attached complete a heterocyclic ring having from 4 to 8 atoms in the ring structure;

R$_{50}$ represents O or S;

R$_{51}$ represents N$_3$, SH, NH$_2$, NO$_2$ or OR'$_7$;

R$_{52}$ represents hydrogen, a lower alkyl, an amine, OR'$_7$, or a pharmaceutically acceptable salt, or R$_{51}$ and R$_{52}$ taken together with the phosphorous atom to which they are attached complete a heterocyclic ring having from 5 to 8 atoms in the ring structure;

Y$_1$ and Y$_2$ independently each represent a hydroxyl group or a group capable of being hydrolyzed to a hydroxyl group, or Y$_1$ and Y$_2$ together, including the boron to which they are bound, form a 5-8 membered cyclic derivative which is capable of being hydrolyzed to hydroxyl groups;

X$_1$ represents a halogen;

X$_2$ and X$_3$ each represent a hydrogen or a halogen;

m is zero or an integer in the range of 1 to 8; and n is an integer in the range of 1 to 8.

10. The method of claim 9, wherein the ring A is represented by the formula:

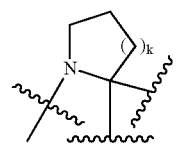

wherein, k is an integer of 1 or 2.

11. The method of claim 9, wherein W represent

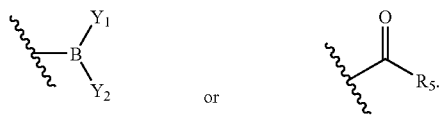

12. The method of claim 9, wherein R$_1$ represents

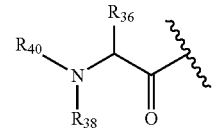

wherein,

R$_{36}$ represents a small hydrophobic group and R$_{38}$ is hydrogen, or, R$_{36}$ and R$_{38}$ together form a 4-7 membered heterocycle including the N and the Cα carbon, as defined for A above; and R$_{40}$ represents a C-terminally linked amino acid residue or amino acid analog, or a C-terminally linked peptide or peptide analog, or an amino-protecting group.

13. The method of claim 9, wherein R$_2$ is absent.

14. The method of claim 9, wherein R$_3$ is a hydrogen.

15. The method of claim 9, wherein R$_5$ is a hydrogen.

16. The method of claim 9, wherein X$_1$ is a fluorine, and X$_2$ and X$_3$, if halogens, are fluorine.

17. The method of claim 9, wherein the inhibitor is represented by Formula (II):

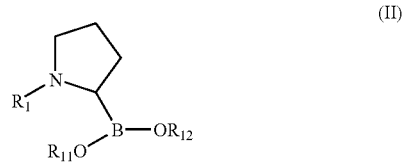

wherein,

R$_1$ represents a C-terminally linked amino acid residue a C-terminally linked amino acid analog, a C-terminally linked peptide, a C-terminally linked peptide analog,

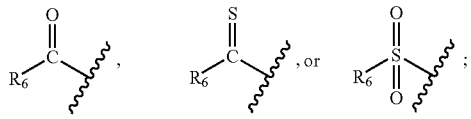

R₇ represents an aryl, a cycloalkyl, a cycloalkenyl, or a heterocycle; and

R₁₁ and R₁₂ each independently represent hydrogen, an alkyl, or a pharmaceutically acceptable salt, or R₁₁ and R₁₂ taken together with the O—B—O atoms to which they are attached complete a heterocyclic ring having from 5 to 8 atoms in the ring structure.

18. The method of claim 9, wherein the inhibitor is represented by Formula III:

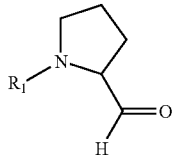

(III)

wherein,

R₁ represents a C-terminally linked amino acid residue a C-terminally linked amino acid analog, a C-terminally linked peptide, a C-terminally linked peptide analog

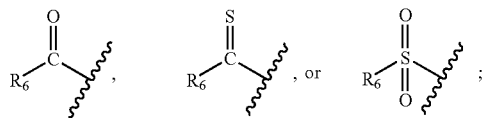

R₇ represents an aryl, a cycloalkyl, a cycloalkenyl, or a heterocycle.

19. The method of claim 1, wherein the inhibitor is represented by the Formula IV:

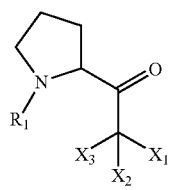

(IV)

wherein,

R₁ represents a C-terminally linked amino acid residue a C-terminally linked amino acid analog, a C-terminally linked peptide, a C-terminally linked peptide analog,

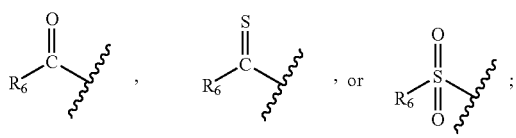

R₆ represents a hydrogen, a halogen, an alkyl, an alkenyl, an alkynyl, an aryl, —(CH₂)ₘ—R₇, —(CH₂)ₘ—OH, —(CH₂)ₘ—O-alkyl, —(CH₂)ₘ—O-alkenyl, —(CH₂)ₘ—O-alkynyl, —(CH₂)ₘ—O—(CH₂)ₘ—R₇, —(CH₂)ₘ—SH, —(CH₂)ₘS-alkyl,
—(CH₂)ₘ—S-alkenyl, —(CH₂)ₘ—S-alkynyl, —(CH₂)ₘ—S—(CH₂)ₘ—R₇,

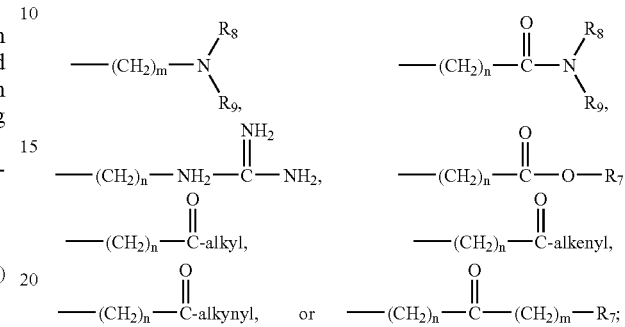

R₇ represents an aryl, a cycloalkyl, a cycloalkenyl, or a heterocycle;

R₈ and R₉ each independently represent hydrogen, alkyl, alkenyl, —(CH₂)ₘ—R₇, —C(=O)-alikyl, —C(=O)-alkenyl, —C(=O)-alkynyl, or —C(=O)—(CH₂)ₘ—R₇, or R₈ and R₉ taken together with the N atom to which they are attached complete a heterocyclic ring having from 4 to 8 atoms in the ring structure;

X₁, X₂ and X₃ each represent a hydrogen or a halogen;

m is zero or an integer in the range of 1 to 8; and n is an integer in the range of 1 to 8.

20. The method of claim 9, wherein the inhibitor is represented by the Formula Xa or Xb:

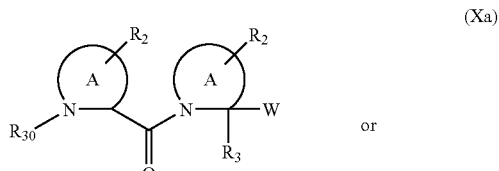

(Xa)

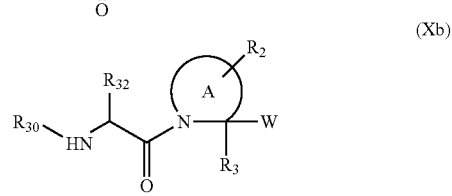

(Xb)

wherein,

A represents a 4- to 8-membered heterocycle including a N and a Cα carbon;

W represents CN, —CHNR₅,

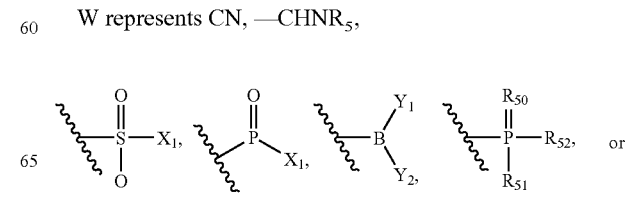

-continued

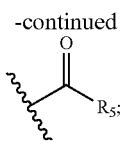

$R_2$ is absent or represents one or more substitutions to the ring A, each of which can independently be a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, or —$(CH_2)_n$—S—$(CH_2)_m$—$R_7$;

$R_3$ represents a hydrogen or a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, or —$(CH_2)_n$—S—$(CH_2)_m$—$R_7$;

$R_5$ represents a hydrogen, an alkyl, an alkenyl, an alkynyl, —$C(X_1)(X_2)X_3$, —$(CH_2)_m$—$R_7$, —$(CH_2)_n$—OH, —$(CH_2)_n$—O-alkyl, —$(CH_2)_n$—O-alkenyl, —$(CH_2)_n$—O-alkynyl, —$(CH_2)_n$—O—$(CH_2)_m$—$R_7$, —$(CH_2)_n$—SH, —$(CH_2)_n$—S-alkyl, —$(CH_2)_n$—S-alkenyl, —$(CH_2)_n$—S-alkynyl, —$(CH_2)_n$—S—$(CH_2)_m$—$R_7$, —$C(O)C(O)NH_2$, or —$C(O)C(O)OR'_7$, $R_7$ represents, for each occurrence, a substituted or unsubstituted aryl, aralkyl, cycloalkyl, cycloalkenyl or heterocyclyl;

$R'_7$ represents, for each occurrence, hydrogen, or a substituted or unsubstituted alkyl, alkenyl, aryl, aralkyl, cycloalkyl, cycloalkenyl or heterocyclyl;

$R_{32}$ is a small hydrophobic group;

$R_{30}$ represents a C-terminally linked amino acid residue or amino acid analog, or a C-terminally linked peptide or peptide analog, or an amino-protecting group;

$R_{50}$ represents O or S;

$R_{51}$ represents $N_3$, SH, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$Y_1$ and $Y_2$ independently represent a hydroxyl group or a group capable of being hydrolyzed to a hydroxyl group, or $Y_1$ and $Y_2$ together, including the boron to which they are bound, form a 5-8 membered cyclic derivative which is capable of being hydrolyzed to hydroxyl groups;

$X_1$ represents a halogen;

$X_2$ and $X_3$ each represent a hydrogen or a halogen;

m is zero or an integer in the range of 1 to 8; and n is an integer in the range of 1 to 8.

21. The method of claim 1, wherein said conjointly administering is achieved by simultaneous dosing of the individual components.

22. The method of claim 1, wherein said conjointly administering is achieved by sequential dosing of the individual components.

23. The method of claim 1, wherein said conjointly administering is achieved by separate dosing of the individual components.

24. The method of claim 1, wherein said conjointly administering is achieved by dosing the individual components in the same composition.

* * * * *

UNITED STATES PATENT AND TRADEMARK OFFICE
CERTIFICATE OF CORRECTION

| | |
|---|---|
| PATENT NO. | : 7,459,428 B2 |
| APPLICATION NO. | : 11/487947 |
| DATED | : December 2, 2008 |
| INVENTOR(S) | : William A. Bachovchin, Andrew G. Plaut and Daniel Drucker |

It is certified that error appears in the above-identified patent and that said Letters Patent is hereby corrected as shown below:

In column 1, at lines 18-20, replace:

"Work described herein was supported by funding from the National Institutes of Health. The United States Government has certain rights in the invention." with --This invention was made with government support under Grant AI040228 awarded by the National Institutes of Health. The government has certain rights in the invention.--

Signed and Sealed this

Twenty-ninth Day of June, 2010

David J. Kappos
*Director of the United States Patent and Trademark Office*